United States Patent [19]

Harper et al.

[11] 4,049,663
[45] Sept. 20, 1977

[54] ETHYLENE DIAMINE DERIVATIVES

[75] Inventors: Norman James Harper, Newcastle-upon-Tyne; George Bryan Austin Veitch, Wythall, both of England

[73] Assignee: Allen & Hanburys Limited, London, England

[21] Appl. No.: 681,853

[22] Filed: Apr. 30, 1976

Related U.S. Application Data

[60] Division of Ser. No. 518,720, Oct. 29, 1974, Pat. No. 3,975,443, which is a continuation of Ser. No. 289,366, Sept. 15, 1972, abandoned.

[30] Foreign Application Priority Data

June 6, 1972   United Kingdom ............... 26248/72

[51] Int. Cl.$^2$ .......................................... C07D 211/06
[52] U.S. Cl. ............................ 260/293.86; 260/293.8; 260/293.88; 260/293.9
[58] Field of Search ............. 424/250; 260/558, 293.8, 260/293.86, 293.88, 293.9

*Primary Examiner*—Stanley J. Friedman
*Attorney, Agent, or Firm*—Bacon & Thomas

[57] ABSTRACT

Compounds of the general formula I:

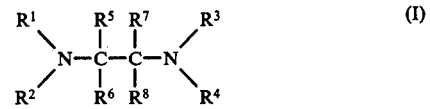

in which $R^1$–$R^4$ which may be the same or different represent hydrogen atoms, or $C_{1-6}$ straight or branched chain alkyl, alkenyl or alkynyl group or an alkyl group substituted by a cycloalkyl group, or represents a cycloalkyl, alkoxycarbonyl, aryl, aralkyl, acyl (which includes arylsulphonyl) groups in which the alkyl group or the alkyl portion of the aralkyl group may be substituted with one or more hydroxy or esterified hydroxy groups and in which the aryl groups or the aryl portion of the acyl or aralkyl group may be substituted by one or more halogen atoms, alkyl groups, hydroxy groups, alkoxy groups, trifluoromethyl, nitro, amino or dialkylamino groups, and in which $R^5$–$R^8$ which may be the same or different represent hydrogen atoms or alkyl groups except that not all groups may be hydrogen, or $R^5$ and $R^6$ or $R^7$ and $R^8$ together represent a carbonyl (=O) oxygen and in any of the pairs of groups $R^1/R^2$, $R^3/R^4$, $R^5/R^6$ and $R^7/R^8$ may represent a carbocyclic or heterocyclic ring system optionally substituted by lower alkyl or aryl groups, said ring being saturated or unsaturated. These compounds have utility as oral analgesics.

4 Claims, No Drawings

ETHYLENE DIAMINE DERIVATIVES

This is a division of application Ser. No. 518,720, filed Oct. 29, 1974, now U.S. Pat. No. 3,975,443, which in turn is a continuation of Ser. No. 289,366 filed Sept. 15, 1972, now abandoned.

The present invention relates to novel substituted ethylene diamines which have been found to have pharmacological activity.

According to the invention therefore, there are provided, as new compounds, compounds of the general formula I:

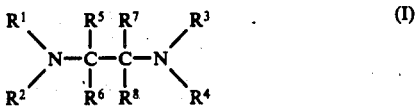

in which $R^1$—$R^4$ which may be the same or different represent hydrogen atoms, or $C_{1-6}$ straight or branched chain alkyl, alkenyl or alkynyl group or an alkyl group substituted by a cycloalkyl group, or represents a cycloalkyl, alkoxycarbonyl, aryl, aralkyl, acyl (which includes arylsuphonyl) groups in which the alkyl group or the alkyl portion of the aralkyl group may be substituted with one or more hydroxy or esterified hydroxy groups and in which the aryl groups or the aryl portion of the acyl or aralkyl group may be substituted by one or more halogen atoms, alkyl groups, hydroxy groups, alkoxy groups, trifluoromethyl, nitro, amino or dialkylamino groups, and in which $R^5$–$R^8$ which may be the same or different represent hydrogen atoms or alkyl groups except that not all groups may be hydrogen, or $R^5$ and $R^6$ or $R^7$ and $R^8$ together represent a carbonyl (= O) oxygen and in any of the pairs of groups $R^1/R^2$, $R^3/R^4$, $R^5/R^6$ and $R^7/R^8$ may represent a carbocyclic or heterocyclic ring system optionally substituted by lower alkyl or aryl groups, said ring being saturated or unsaturated.

The term acyl as used herein means the residue of an organic acid and includes in particular benzoyl, formyl and acetyl. In the context of this specification it is also intended to extend to arylsulphonyl and references to acylation are to be construed accordingly. The term aryl as used herein means an aromatic or heteroaromatic nucleus.

The invention extends to the non-toxic salts of the compounds defined above in particular acid addition salts, such as the hydrochloride, sulphate, maleate and tartrate.

Since some of the compounds can exist in optically active form the invention also extends to such isomers and mixtures thereof.

This is particularly the case with the open chain compounds processing at least one asymmetric carbon atom.

A preferred group of compounds according to the invention are those in which the groups $R^7$ and $R_8$ together with the adjacent carbon atom form a carbocyclic ring system particularly one containing from 4 to 7 carbon atoms, such as cyclopentyl and in particular cyclohexyl. The groups $R^3$ and $R^4$ preferably represent alkyl or alkenyl or alkynyl groups containing from 1 to 6 carbon atoms preferably 1 to 4 carbon atoms in the case of alkyl and alkynyl such as methyl, allyl, propargyl of dimethylallyl but can represent hydrogen or aralkyl in particular phenethyl or benzyl, or cyclopentyl or together with the adjacent nitrogen atom, form a heterocyclic ring system of which ring systems, piperdyl, N-methyl-piperazinyl and pyrrolidinyl are representative. The groups $R_1$ and $R^2$ preferably represent hydrogen, $C_{1-4}$ alkyl, in particular methyl, acyl, in particular formyl (HCO—) and benzoyl which may be substituted by fluorine or chlorine in the aryl portion or aralkyl, in particular benzyl, which may be substituted in the alkyl ($CH_2$—) portion thereof by hydroxy or esterified, particularly acetylated, hydroxy groups. Preferably the group $R^5$ and $R^6$ represent hydrogen or $C_{1-4}$ alkyl in particular methyl.

In another specific group of compounds $R^7$ and $R^8$ as well as $R^5$ and $R^6$ preferably represent hydrogen or $C_{1-4}$ alkyl except that not all these groups can simultaneously be hydrogen. Particularly preferred compounds are those in which one of $R^7$ and $R^8$ both represent $C_{1-4}$ alkyl in particular methyl and one of $R^5$ and $R^6$ represent hydrogen, the other of $R^5$ and $R^6$ representing $C_{1-4}$ alkyl, in particular methyl, or hydrogen.

A particular sub-class of compounds within this other specific group of compounds are these of the general formula:

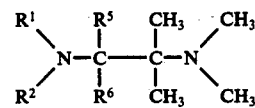

in which
$R^1$ represents benzoyl, chloro substituted benzoyl or COOAlk, in which Alk is $C_{1-4}$ alkyl group.
$R^2$ represents hydrogen or methyl.
$R^5$ represents methyl.
$R^6$ represents hydrogen.

Particularly preferred classes of compounds according to the invention are those specified below.

1. Compounds in which $R^1$ represents one of the following acyl groups, 3,4-dichlorobenzoyl, formyl, benzoyl, 4-fluorobenzoyl, 4-chlorobenzoyl, 3,4-di-ethoxybenzoyl, 4-methylbenzoyl, 2-chlorobenzoyl, acetyl, p-toluene sulphonyl, 2,3,4-trimethoxybenzoyl, 3,4-dichlorobenzoyl sulphonyl, 2,4-dichlorobenzoyl; or represents hydrogen or methyl or ethyl.
$R^2$ represents a hydrogen or a methyl group.
$R^3$ represents a methyl group.
$R^4$ represents a methyl group or a benzyl group or represents a hydrogen atom.
$R^5$ and $R^6$ represent hydrogen and/or methyl.
$R^7$ and $R^8$ together form a cyclohexyl group.

2. Compounds in which $R^1$ represents a hydrogen atom; or one of the following acyl groups, formyl, acetyl, 4-fluorobenzoyl, 2-chlorobenzoyl, 3,4-dichloro benzoyl, 2,3,4-trimethoxy benzoyl, 4-nitro-benzoyl, 4-aminobenzoyl, or represents an ethoxycarbonyl group; or represents methyl or ethyl;
$R^2$ represents hydrogen or methyl.
$R^5$ and $R^6$ represent hydrogen.
$R^7$ and $R^8$ together form a cyclohexyl group.
$R^3$ and $R^4$ together with the adjacent nitrogen atom form a piperidyl group.

3. Compounds in which $R^1$ represents a hydrogen atom, or one of the following acyl groups, formyl, acetyl, 3,4-dichlorobenzoyl, 2,3,4-trimethoxybenzoyl, p-toluene sulphonyl, 2,4-dichlorobenzoyl; or a methyl or ethyl group;
$R^2$ represents a hydrogen atom, a formyl group or a methyl group;

$R^5$ represents a hydrogen atom or a phenyl group;

$R^6$ represents a hydrogen atom;

$R^3$ and $R^4$ form, together with the adjacent nitrogen atom a 4-methyl-piperazinyl group; and $R^7$ and $R^8$ together form a cyclohexyl group.

4. Compounds in which $R^1$ represents a hydrogen atom or one of the following acyl groups, 3,4-dichlorobenzoyl, 2-chlorobenzoyl and benzoyl; or an ethoxycarbonyl group;

$R^2$ represents a hydrogen atom or a methyl group;

$R^3$ represents a methyl group;

$R^4$ represents a hydrogen atom or methyl, benzyl, allyl, propynyl, dimethylallyl, cyclopropylmethyl, phenethyl;

$R^5$ represents hydrogen or methyl;

$R^6$ represents hydrogen;

$R^7$ represents methyl; and $R^8$ represents methyl or butyl.

Specific preferred compounds are those the preparation of which is described in the Examples.

The compounds according to the invention may in principle be prepared from an aminonitrile of the formula:

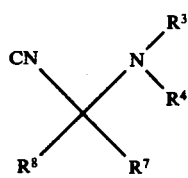

(II)

in which $R^3$, $R^4$, $R^7$ and $R^8$ have the above stated meanings. This aminonitrile may be prepared from a parent ketone by the standard Strecker synthesis as exemplified below with reference to cyclohexanone.

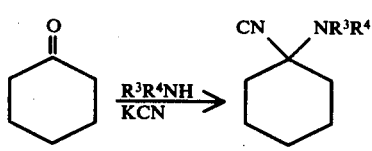

In this synthesis the parent ketone is reacted with an amine of the formula $R^3R^4NH$, in which $R^3$ and $R^4$ have the meanings given above, or an acid addition salt thereof, in the presence of HCN or KCN.

The aminonitrile II is then converted into the amine III below:

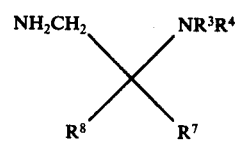

(III)

This conversion is preferably effected in one of two ways. According to the first method the aminonitrile is reduced directly to the amine, for example with a complex metal hydride such as $LiAlH_4$ or Raney nickel/hydrogen. Another reducing agent which may be used in sodium aluminium bis methoxyethoxy hydride. According to the second method the aminonitrile may first be hydrolysed to the amide, which represent compounds according to the invention in which $R^5$ and $R^6$ together represent a carbonyl oxygen (C=O) for example with concentrated sulphuric acid which amide may then subsequently be reduced to the amine by a chemical reducing agent such as $LiAlH_4$.

The above described process is appropriate for the preparation of compounds in which $R^1$ and $R^2$ and $R^5$ $R^6$ are hydrogen. These compounds may be further acylated to produce compounds in which $R^1$ and/or $R^2$ have meaning other than hydrogen. Acylation may be effected in a conventional manner. Thus, for example, where $R^1$ represents an acyl group the amine may be treated with an acylating agent providing such a group $R^1$, for example an acid chloride, or an aryl sulphonyl chloride where $R^1$ is an arylsulphonyl group. Acylation, for example formylation may also be carried out using formic acid and acetic anhydride to convert the group $R^1=H$ to $R^1=OHC-$ (formyl). If the resulting formyl compound is reduced for example with $LiAlH_4$ the formyl group is converted to the methyl group and in this one obtains a compound in which $R^1$ is an alkyl group. The monomethylamino compound can then be formylated once again to give the compound in which $R^1 = CH_3$ and $R^2=OHC$. The scheme below shows an example of such a reaction.

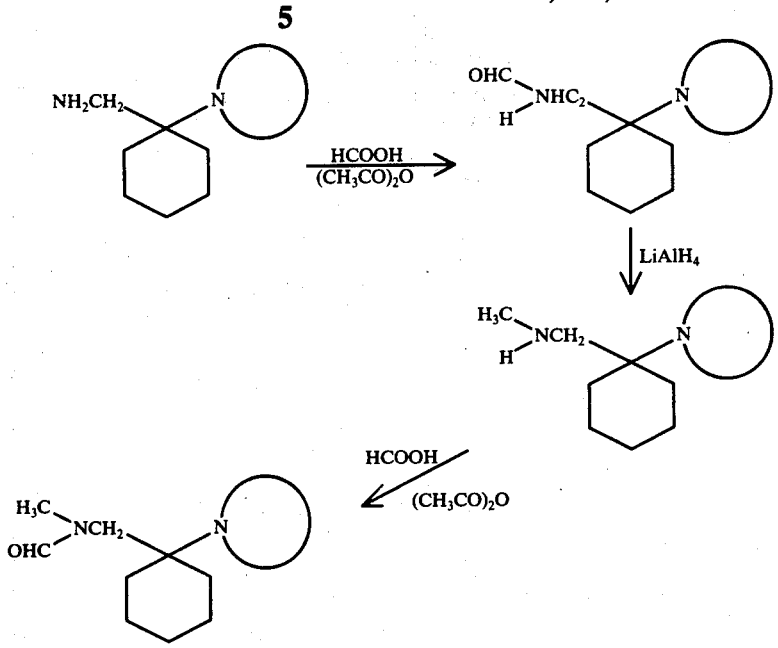

This reaction is applicable to the other acylated compounds, and thus for example the acetylation may be effected to give the corresponding acetyl compound which may then be reduced to convert the acetyl group to the ethyl group. The above reaction is therefore of general applicability for the conversion of $R^1/R^2 =$ acyl to $R^1/R^2 =$ alkyl.

In an alternative process starting with the nitrile II for the production of compounds in which $R^5$ is an alkyl group and $R^6$ is a hydrogen atom, the nitrile may be reacted with a metal alkyl for example a lithium alkyl to give an intermediate imine which may then be reduced to the primary amine by chemical or catalytic reduction, for example with $LiAlH_4$ or Raney nickel/hydrogen. This process is shown diagrammatically below.

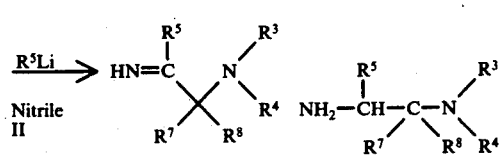

This results in compounds in which $R^1$ and $R^2$ are hydrogen. This compound may be acylated (and alkylated) as described above. Compounds in which any of $R^1$ to $R^4$ are alkoxycarbonyl may be prepared by acylation with a haloacid ester such as chloroformic acid ester and the term acylation extends to such reaction.

Where the groups $R^1$ or $R^2$ is an aralkyl group in particular benzyl with an hydroxy group substitutent in the alkyl fragment the compound may be prepared by reduction of the parent amide to reduce $C=O$ to $CHOH$. The OH group may be acylated to produce the corresponding ester.

The nature of the groups $R^3$ and $R^4$ may be the same as in the starting moiety providing that moiety of the compound. However, it is possible to convert the groups $R^3$ and $R^4$ into other groups within the meanings given after production of a compound according to the invention. Thus, where either of $R^3$ and $R^4$ are hydrogen they may be acylated or alkylated as described above for $R^1$ and $R^2$ provided that the group $NR^1R^2$ is itself not capable of being alkylated or acylated. Alkylation may also be effected subject to this proviso with a halide such as an alkyl or aralkyl halide to yield the group $R^3$ or $R^4$ (other than hydrogen). Compounds in which $R^3$ and/or $R^4$ are hydrogen are conveniently prepared by debenzylation of those compounds in which these groups are benzyl. Also where an acyl group contains a nitro group e.g. p-nitro benzoyl, this may be reduced to an amine group subsequently.

The invention therefore further provides a process for the production of compounds according to the invention which comprises converting an aminonitrile of the formula II

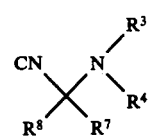 (II)

in which $R^3$, $R^4$, $R^7$ and $R^8$ have the above stated meanings into an amine of the general formula III

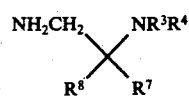 (III)

by direct reduction or for the production of compounds in which $R^5$ and $R^6$ represent a carbonyl group hydrolysing the compound of formula II to the amide;

or for the production of compounds in which $R^5$ and $R^6$ represent hydrogen reducing the amide to the amine;

or for the production of compounds in which $R^1$ is an acyl group acylating said amine III with a compound yielding said acyl group;

or for the production of compounds in which $R^1$ is alkyl reducing said acyl group to an alkyl group;

or for the production of compounds in which $R^2$ is an acyl group acylating the resultant monoalkylamine with a compound yielding said acyl group $R^2$;

or for the production of a compound in which both $R^1$ and $R^2$ are alkyl reducing the monoacylated monoalkylamine;

or for the production of compounds in which $R^5$ is other than hydrogen reacting the aminonitrile II specified above with an alkyl lithium $R^5Li$ and reducing the thus formed imine to form the primary amine;

or for the production of compounds in which $R^5$ is alkyl, and $R^1$ is acyl or alkyl and/or $R^2$ is hydrogen or acyl or alkyl, acylating the above primary amine ($R^5$ = alkyl) if desired with subsequent reduction of the acyl groups;

or for the production of compounds in which $R^1$ or $R^2$ represents an aralkyl group in which the alkyl portion is substituted by a hydroxy group reducing the parent amide to convert to C=O to CHOH;

or for the production of compounds in which $R^1$ or $R^2$ represent an aralkyl group with an esterified hydroxyl group in the alkyl side chain acylating the compound in which the alkyl group contains a hydroxy group;

or for the production of compounds in which $R^3$ or $R^4$ is hydrogen debenzylating the corresponding compound in which $R^3$ or $R^4$ represents a benzyl group;

or for the production of compounds in which $R^3$ and/or $R^4$ are other than hydrogen acylating or alkylating a compound of formula I in which the group $NR^1R^2$ is not capable of being acylated or alkylated, and if desired with subsequent conversion of any of the groups $R^1$ to $R^8$ to groups having either of the above given meanings and if desired isolating the product as an acid addition salt.

The compounds according to the invention show good activity as oral analgesics. They may be formulated for administration in association with any suitable pharmaceutically acceptable carrier. The formulations may be liquid or solid and may be suitable for oral or parenteral administration or other route. Preferred formulations include capsules, tablets, which may be coated, injections, liquid oral dosage forms, suppositories etc. A preferred dosage is parenterally from 10–500 mg. and orally from 8–500 mg.

The following Examples illustrate the invention:

EXAMPLE 1

1-(3,4-Dichlorobenzamidomethyl)-cyclohexyldimethylamine (a) 1-Cyanocyclohexyldimethylamine Dimethylammonium chloride (81.5 g, 1.0 mole) dissolved in water (150 ml.) was added to cyclohexanone (98.0 g., 1.0 mole), quickly followed by a solution of potassium cyanide (68.0 g, 1.045 mole) in water (150 ml.) added over a period of five minutes. The reaction mixture was stirred for 24 hours during which time a colourless crystalline solid was formed. The solid was filtered off, washed with ice cold water (200 ml.), dissolved in benzene (150 ml.) and rewashed with water (100 ml.). The aqueous layer was extracted with benzene (100 ml.), the benzene solutions then being combined, dried over anhydrous sodium sulphate and evaporated under reduced pressure. The oily residue (144 g.) solidified to give 1-cyanocyclohexyldimethylamine, m.p. 36°.

(b) 1-Aminomethylcyclohexyldimethylamine

1-Cyano-1-cyclohexyldimethylamine (22.7 g, 0.15 mole) was dissolved in dry ether (200 ml.) and added dropwise to a stirred suspension of lithium aluminium hydride (11.37 g, 0.3 mole) in dry ether (300 ml.). The suspension was stirred overnight and excess lithium aluminium hydride decomposed by dropwise addition of water (28 ml.) and 30% sodium hydroxide solution (21 ml.) followed by water (50 ml.). The ether layer was separated, dried ($Na_2SO_4$), and evaporated to yield a colourless, mobile oil (21.4 g, 92.5%). Addition of 10% ethanolic HCl to an ethereal solution of the oil gave a solid which was recrystallised from ethanol/ether as colourless needles of 1-aminomethylcyclohexyl dimethylamine dihydrochloride m.p. 251°–3°.

EXAMPLE 2

1-(3,4-Dichlorobenzamidomethyl)-cyclohexyldimethylamine

A mixture of 1-aminomethylcyclohexyl dimethylamine (1.0 g.), 3,4-dichlorobenzoyl chloride (2 ml) and pyridine (10 ml) was allowed to stand at room temp. for 1 hr. The pale yellow solid produced was filtered and recrystallised from ethanol/ether to give colourless microneedles of 1-(3,4-dichlorobenzamidomethyl)-cyclohexyldimethylamine hydrochloride m.p. 215°–16°.

EXAMPLE 3

N-formylaminomethyl-cyclohexyl-dimethylamine

A solution of chloral (4.7 g.) in chloroform (30 ml) was added dropwise to a stirred and cooled solution of 1-aminomethylcyclohexyl-dimethylamine (2) (5 g.) in chloroform (30 ml). The mixture was stirred for 64 hrs. and then heated in a steam bath for 0.5 hrs.

The excess chloroform was evaporated under reduced pressure and the oily residue distilled under high vacuum to give N-formylaminomethylcyclohexyl dimethylamine (6.0 g.) b.p. 120° C at 0.7 mm Hg.

EXAMPLE 4

1-Benzamidomethylcyclohexyldimethylamine

A mixture of 1-aminomethylcyclohexyldimethylamine (1.5 g), benzoyl chloride (3 ml) and pyridine (10 ml) was allowed to stand at room temperature for 1 hr. The crystalline mass was filtered and recrystallised several times from 95% ethanol to give colourless prisms of 1-benzamidomethylcyclohexyldimethylamine hydrochloride m.p. 245°–6°.

EXAMPLE 5

1-(4-Fluorobenzamidomethyl) cyclohexyldimethylamine

A mixture of 1-aminomethylcyclohexyldimethylamine (1.0 g), 4-fluorobenzoyl chloride (2 ml) and pyridine (10 ml) was allowed to stand at room temperature for 1 hr. The crystalline material produced was filtered and recrystallised several times from ethanol/ether to give colourless needles of 1-(4-fluorobenzamidomethyl)-cyclohexyl dimethylamine hydrochloride m.p. 238°–239°.

EXAMPLE 6

4-Chlorobenzamidomethyl-cyclohexyl dimethylamine

A solution of 4-chlorobenzoylchloride (1 g.) and 1-aminomethylcyclohexyl-dimethylamine (1.8 g.) in benzene (100 ml.) was heated under reflux for 0.5 hours on a steam bath. The excess benzene was removed under reduced pressure and the oily residue was dissolved in water and extracted with chloroform (4 × 40 cm³). The chloroform extracts were dried (anhyd. sodium sulphate) and the chloroform removed under reduced pressure to give a white solid (1.6 g. m.p. 97°–99°).

The solid was dissolved in chloroform (60 ml.) and washed with 2N sodium carbonate (2 × 40 ml). The chloroform extract was dried (anhyd. sodium sulphate) and the chloroform evaporated under reduced pressure. The solid residue was crystallised from petroleum ether (60°–80° C) to give 4-Chlorobenzamidomethyl cyclohexyl dimethylamino (1.5 g.) m.p. 105°–7°.

EXAMPLE 7

3,4-Dimethoxy-benzamidomethyl-cyclohexyl-dimethylamine

A solution of 3,4 dimethoxybenzoyl chloride (1.28 g.) and 1-aminomethyl-cyclohexyl dimethylamine (1 g.) in benzene (100 ml.) were heated under reflux for 1.5 hours. The excess benzene was evaporated under reduced pressure and the residue dissolved in water and made alkaline. The aqueous solution was extracted with chloroform (4 × 40 ml), the chloroform solution was extracted with 2N hydrochloric acid (2 × 15 ml) and the excess water was evaporated under reduced pressure. The solid residue was crystallised from ethanol to give 3,4-dimethoxy benzamidomethyl cyclohexyl dimethylamine hydrochloride (0.5 g.) m.p. 227°–229°.

EXAMPLE 8

4-Methylbenzamidomethyl-cyclohexyl dimethylamine hydrochloride

A solution of p-toluoyl chloride (1 g.) 1-aminomethyl-cyclohexyl dimethylamine (1 g.) and triethylamine (0.65 g.) in benzene (60 ml.) was heated under reflux for 1.5 hrs. The excess benzene was evaporated under reduced pressure, the residue dissolved in water and extracted with chloroform. The extracts were dried (anhyd. sodium sulphate) and the chloroform evaporated under reduced pressure to give an oil which solidified on cooling. Excess ethereal hydrochloric acid was added to an ethereal solution of the solid and the excess ether removed under reduced pressure. The solid residue was crystallised from isopropanol/petroleum ether (80–100) to give 4-methylbenzamido methyl cyclohexyl dimethylamine hydrochloride m.p. 199°–201° (0.7 g.).

EXAMPLE 9

3-Chlorobenzamidomethyl-cyclohexyl dimethylamine hydrochloride

A solution of 1-aminomethyl-cyclohexyl dimethylamine (1 g.) and m-chlorobenzoyl chloride (1.12 g.) in benzene (60 ml.) was heated under reflux for three hours. The precipitate was filtered and crystallised from ethanol/isopropanol to give 3-chlorobenzamido-cyclohexyl-dimethylamine hydrochloride (2.0 g.) m.p. 233°–235°.

EXAMPLE 10

2-Chlorobenzamidomethyl cyclohexyl dimethylamine hydrochloride

A solution of 1-aminomethyl cyclohexyl dimethylamine (1 g.) and o-chlorobenzoylchloride (1.12 g.) in benzene (60 ml.) was heated under reflux for 3 hrs. The precipitate was filtered and crystallised from isopropanol to give 2-chlorobenzamido-methyl-cyclohexyl-dimethylamine hydrochloride (1.3 g.) m.p. 229°–231°.

EXAMPLE 11

Acetamidomethyl cyclohexyl dimethylamine

A mixture of acetic anhydride (50 ml.) and 1-aminomethylcyclohexyl dimethylamine (6 g.) was heated on a steam bath for one hour. The excess acetic anhydride was evaporated under reduced pressure. Ether (75 ml) 5N sodium hydroxide (10 ml) and sodium hydroxide (1 g.) was added to the mixture. Anhydrous sodium carbonate was added and the mixture was filtered after 60 mins. The excess ether was evaporated under reduced pressure to give an oily residue (7.1 g.). 3 g. of this oil was distilled under high vacuum to give accianidomethylcyclohexyldimethylamine (2.6 g.) b.p. 120° C at 0.1 mm Hg.

EXAMPLE 12

4-Toluenesulphonamidomethylcyclohexyldimethylamine hydrochloride

A solution of toluene-4-sulphonyl chloride (1.22 g) and 1 amino methyl cyclohexyl dimethylamine (1 g.) in benzene (60 ml) was heated under reflux for 45 mins. The precipitate was filtered and crystallised from ethanol to give p-toluene sulphonamidomethylcyclohexyldimethylamine hydrochloride (1.9 g) m.p. 226°–228° C.

EXAMPLE 13

1-[1-(3,4,5-Trimethoxybenzamidomethyl)cyclohexyl]-dimethylamine hydrochloride

Solutions of 3,4,5-trimethoxybenzoylchloride (1.5 g.) in benzene (25 ml.) and aminomethyl cyclohexyldimethylamine (1.0 g.) in benzene (25 ml.) were mixed and heated under reflux for 1 1/2 hrs. The solid which separated was filtered, washed with benzene and crystallized from isopropanol to give 1-[1-(3,4,5-trimethoxybenzamidomethyl) cyclohexyl]dimethylamine hydrochloride (1.6 g. 65%) m.p. 198°–9°.

EXAMPLE 14

3,4-Dichloro-[aminomethylcyclohexyldimethylamine]-benzenesulphonamide hydrochloride Solutions of aminomethyl cyclohexyldimethylamine (1.0 g.) in dry benzene (15 ml.) and 3,4-dichlorobenzenesulphonyl chloride (1.57 g.) in dry benzene (15 ml.) were mixed and heated under reflux on a steam bath for one hour. The reaction mixture was cooled, filtered and the residue was washed with benzene and dried. This solid was crystallised from isopropanol to give 3,4-dichloro-[1-(dimethylamino)cyclohexanemethyl]benzenesulphonamide hydrochloride (1.9 g. 74%) m.p. 206°.

EXAMPLE 15

1-1′-Hydroxybenzyl-methylaminomethylcyclohexyl-dimethylamine

1-Benzamidomethylcyclohexyldimethylamine (6.3 g, 0.025 mole) was dissolved in dry benzene (100 ml) and added dropwise to a stirred suspension of lithium aluminium hydride (1.9 g, 0.05 mole) in dry ether (200 ml.). The suspension was refluxed overnight and excess lithium aluminium hydride decomposed by dropwise addition of water (4 ml), 50% sodium hydroxide solution (3 ml), and water (14 ml). The ether/benzene layer was separated, washed with water, dried (Na$_2$SO$_4$), and evaporated to yield an amber, mobile oil (5.43 g, 86.2%). On treatment with ethanol/iodomethane the oil gave colourless crystals of 1-1'-hydroxybenzyl-methylaminomethylcyclohexyl trimethylammonium diiodide m.p. 194°-195°. (decomp) (from ethanol/ether).

EXAMPLE 16

1-1'-Acetoxybenzyl-methylaminomethylcyclohexyl-dimethylamine 1-1'-Hydroxybenzyl-methylaminomethylcyclohexyldimethylamine (1.5 g. 0.0057 mole) was refluxed for 3 hr. with acetic anhydride (5 ml) in pyridine (5 ml). The solvent was evaporated under reduced pressure and the residue azeotroped to give a brown, viscous oil (1.1 g, 63.2%). On treatment with 10% ethanolic hydrochloric acid and storage in a refrigerator for 2 days this oil yielded pale buff prisms of 1-1'-acetoxybenzylmethylaminomethylcyclohexyldimethylamine hydrochloride m.p. 177°-178°. (from ethanol/ether)

EXAMPLE 17

1-Methylaminomethylcyclohexyldimethylamine

N-Formylaminomethylcyclohexyldimethylamine prepared as in Example 3 (9.0 g. 0.05 mole) was dissolved in dry ether (100 ml) and added dropwise to a stirred suspension of lithium aluminium hydride (3.8 g. 0.1 mole) in dry ether (200 ml). The suspension was refluxed for 24 hr. and excess lithium aluminium hydride decomposed by dropwise addition of water (8 ml), 30% sodium hydroxide solution (6 ml), and water (28 ml). The ether layer was separated, dried (Na$_2$SO$_4$), and evaporated to give a colourless mobile oil (7.8 g. 94.2%). An aliquot of this oil was treated with 10% ethanolic hydrochloric acid to give colourless needles of N-methylaminomethylcyclohexyldimethylamine dihydrochloride, m.p. 232°-233°(from ethanol/ether).

EXAMPLE 18

1-(Dimethylamino)-cyclohexyl)-N-ethylmethylaminedihydrochloride

A solution of acetamidomethylcyclohexyl-dimethylamine (4g.) in tetrahydrofuran (30 ml) was added dropwise to a cooled and stirred suspension of lithium aluminium hydride (1.0 g.) in tetrahydrofuran and the mixture was heated under reflux for 24 hrs. The suspension was cooled in ice and the excess lithium aluminium hydride decomposed with water.

The suspension was dried with anhydrous sodium sulphate. The mixture was filtered (hyflo) and the residue washed thoroughly with ether. The combined ethereal extracts were extracted with 2N hydrochloric acid (3 × 15 ml), the acid solution was evaporated under reduced pressure and the solid residue crystallized from ethanol/isopropanol to give 1-(dimethylamino)-cyclohexyl)-N-ethyl-dimethylamine hydrochloride (3.5 g) m.p. 239°-241° C.

EXAMPLE 19

1-(N-Formyl-1-methylaminomethyl)cyclohexyldimethylamine

Formic acid (6.9 g. 0.15 mole) and acetic anhydride (15.3 g, 0.15 mole) were mixed without cooling and kept at room temperature for 1 hr. 1-methylaminomethylcyclohexyldimethylamine (5.9 g, 0.034 mole) was dissolved in formic acid (12 ml) and the formylating mixture (16 ml) added slowly. This produced vigorous effervesence and a temperature rise to 75°. The mixture was then left at room temperature for 2 hr. and then heated on a water bath at 55° for 0.75 hr. The solvents were removed under reduced pressure to give an amber oil (5.32 g, 77.7%) which crystallised as colourless prisms of 1-(N-formyl-1-methylaminomethyl) cyclohexyldimethylamine from light petroleum (b.p. 60°-80°), m.p. 59°-60°.

EXAMPLE 20

N-methyl-acetamido-methyl-1-dimethylamino cyclohexane 5N sodium hydroxide (5 cm$^3$) was added to a solution of 1-methylaminomethylclyclohexyldiamethylaminodihydrochloride prepared as in Example 17 (2 g.) in water (2 ml). Benzene (50 cm$^3$) and excess anhyd. sodium sulphate were added and the mixture was filtered.

Acetic anhydride (40 ml) was added to the benzene solution and the mixture was heated under reflux for one hour. The excess acetic anhydride and benzene were evaporated under reduced pressure to give a solid residue. This was made alkaline with excess of a saturated solution of sodium carbonate, ether (50 ml) was added followed by excess anhydrous sodium carbonate to remove the water. The mixture was filtered and the excess ether evaporated under reduced pressure to give an oily residue which was crystallised from petroleum ether (80°-100° C) to give N-methyl-acetamido-methyl-1-dimethylamino-cyclohexane (0.45 g.) m.p. (69°-71°).

EXAMPLE 21

3,4Dichloro-N-methylbenzamidomethylcyclohexyl-dimethylamine hydrochloride 5N sodium hydroxide (3 ml) was added to a solution of methylaminomethyl cyclohexylidimethylamine dihydrochloride (1.16 g) in water (1 ml). Benzene (50 ml) and excess anhyd. sodium sulphate were added, the mixture was filtered and the benzene solution added to a solution of 3,4-dichlorobenzoyl chloride (1 g.) in benzene (20 ml). The solution was heated under reflux for 45 mins. and left to stand for 2 days. The crystalline solid which appeared was filtered to give 3,4-dichloro-N-methyl-benzamido-methyl cyclohexyldimethylamine hydrochloride (1.1 g.) m.p. 189°-192° C.

EXAMPLE 22

1-[1-(3,4,5-trimethoxy-N-methyl-N-{1-(dimethylamine)cyclohexyl]methyl} benzamide hydrochloride

[1-(methylaminomethyl)cyclohexyl]dimethylamine dihydrochloride (1.5 g) was made alkaline with 5N NaOH (5.0 ml). Benzene (20 ml) was added and the basic solution dried (anhyd. Na$_2$CO$_3$). The solution was filtered and the sodium carbonate residue washed with benzene and 3,4,5-trimethoxybenzoyl chloride (1.42 g.) in dry benzene (25 ml) was added. The mixture was heated under reflux for 1¼ hrs. The solid which separated was filtered, and washed with benzene and crystallised from benzene to give 1-[1-(3,4,5-trimethoxy-N-methyl-N-{1-(dimethylamine)cyclohexyl] methyl} benzamide hydrochloride (1.5 g. 61%) m.p. 197° C.

EXAMPLE 23

1-Dimethylaminomethylcyclohexyldimethylamine 1-(N-formyl-1-methylaminomethyl) cyclohexyldimethylamine (2.88 g. 0.014 mole) prepared as in Example 19 was dissolved in dry ether (40 ml) and added dropwise to a stirred suspension of lithium aluminum hydride (1.14 g. 0.03 mole) in dry ether (150 ml). The suspension was stirred overnight and excess lithium aluminum hydride decomposed by dropwise addition of water (3 ml) 30% sodium hydroxide solution (2 ml) and water (10 ml). The ether layer was separated, dried ($Na_2SO_4$), and evaporated to give a pale amber oil (2.34 g. 87.6%). Treatment of this oil with 10% ethanolic hydrochloric acid gave colourless needles of 1-dimethylaminomethyl-1-cyclohexyl dimethylamine dihydrochloride m.p. 232°-4° (from ethanol/ether).

EXAMPLE 24

3,4-Dichloro-[1-(dimethylamino)-α-methylcyclohexanemethyl]-benzamide

To 1-Dimethylamino)cyclohexylmethylimine (35.8 g) was added a suspension of lithium aluminium hydride (12 g.) in dry dioxan (ca. 40 ml) and the mixture was heated under reflux for 5½ hrs. The excess lithium aluminium hydride was neutralised with water and the residue was filtered (hyflo). The filtrate was extracted with 2NHCl (50 ml) and the acid extract evaporated to dryness. The residue was dissolved in water (10 ml) the solution was made alkaline with 5N NaOH (10 ml) and ether (30 ml) was added followed by excess anhyd. $Na_2CO_3$. The solution was filtered, the filtrate was dried (anhyd. $Na_2SO_4$) and evaporated to an oil which was distilled to give 1-(Dimethylamino)-α-methylcyclohexanemethylamine b.p. 12 mm 105°-115° (10.70 g. 30%).

To a solution of 1-(Dimethylamino)-α-methyl cyclohexanemethylamine (1 g.) in dry benzene (15 ml) was added a solution of 3,4-Dichloro-benzoylchloride (1.23 g.) in dry benzene (15 ml) and the mixture was heated under reflux on a steam bath for 1 hr. The benzene was evaporated, the residue was made alkaline with 2N NaOH and extracted with chloroform (×3). The combined chloroform extracts were dried (anhyd. $Na_2SO_4$) and evaporated to an oil which was dissolved in hot light petroleum (60°-80°), decolourised with charcoal and on cooling gave 3,4-Dichloro-[1-(dimethylamino)-α-methylcyclohexanemethyl]benzamide. (1.25 g. 62%) m.p. 111°-114°.

EXAMPLE 25

2,4-Dichloro-[1-(dimethylamino)-α-methylcyclohexanemethyl]-benzamide

To a solution of 1-(Dimethylamino)-α-methylcyclohexanemethylamine (1 g.) in dry benzene (15 ml) was added a solution of 2,4-Dichlorobenzoylchloride (1.23 g.) in dry benzene (15 ml) and the mixture was heated under reflux for 1 hr. The benzene was evaporated, the residue was made alkaline with 2N NaOH and extracted with chloroform (×3). The combined chloroform extracts were dried (anhyd. $Na_2SO_4$) and evaporated to an oil which was dissolved in hot light petroleum (60°-80°), decolourised with charcoal and on cooling gave 2,4-Dichloro-[1-(dimethylamino)-α-methylcyclohexanemethyl]-benzamide (0.9 g. 44%) m.p. 123°-126°.

EXAMPLE 26

3,4-Dichloro-[1-(Dimethylamino)-α-methylcyclohexanemethyl]-benzene sulphonamide

To a solution of 1-(Dimethylamino)-α-methylcyclohexane-methylamine (1 g.) in dry benzene (15 ml) was added a solution of 3,4-Dichlorobenzene sulphonyl chloride (1.23 g.) in dry benzene (15 ml) and the mixture was heated under reflux on a steam bath for 1 hr. The benzene was evaporated, the residue was made alkaline with 2N NaOH and extracted with chloroform (×3). The combined chloroform extracts were dried (anhyd. $Na_2SO_4$) and evaporated to an oil which was dissolved in hot light petroleum (80°-100°), decolourised with charcoal and on cooling gave 3,4-Dichloro-[1-(dimethylamino)-α-methylcyclohexane methyl]-benzene sulphonamide (0.88 g. 40%) m.p. 111°-115°.

EXAMPLE 27

2-Chloro-[1-(dimethylamino)-α-methylcyclohexanemethyl] benzamide hydrochloride

A solution of 1-(dimethylamino)-α-methylcyclohexane-methylamine (1 g.) in dry benzene (15 ml) and a solution of 2-chlorobenzoyl chloride (1.03 g) in dry benzene (15 ml) were mixed and heated under reflux for 1 hr. The solid which separated on cooling was filtered and crystallised from isopropanol to give 2-chloro-[1-(dimethylamino)-α-methylcyclohexanemethyl]benamide hydrochloride (0.9 g 45%) m.p. 227°-228°.

EXAMPLE 28

3,4-Dichloro-N-methyl-N-[1-(dimethylamino)-α-methylcyclohexanemethyl]benzamide hydrochloride Solutions of 1-(dimethylamino)-N, α-dimethylaminocyclohexanemethylamine (1 g.) in benzene (15 ml) and 3,4-dichloro-benzoyl chloride (1.14 g.) in benzene (15 ml) were mixed and heated under reflux for 1 hr. The solid which separated on cooling was filtered, dried and crystallised from isopropanol to give 3,4-dichloro-N-methyl-N-[1-(dimethylamino)-α-methylcyclohexanemethyl]benzamide hydrochloride (0.5 g. 24%) m.p. 212°.

EXAMPLE 29

2-Chloro-N-Methyl-N-[1-(dimethylamino)-α-methylcyclohexanemethyl]benzamide hydrochloride A solution of 1-(dimethylamino)-N,2-dimethylcyclohexane methylamine (1 g.) in benzene and a solution of 2-chlorobenzoyl chloride (0.97 g.) was mixed and heated under reflux for 1 hr. The solid which separated on cooling was filtered to give a deliquescent solid which was dissolved in water (50 ml) and made alkaline with 5N NaOH. The suspension was extracted with chloroform (3 × 50 ml), the combined chloroform extracts washed with water (50 ml) and dried (anhyd. $Na_2SO_4$). The chloroform was evaporated, the residue was dissolved in hot light-petroleum (b.p. 80°-100°), treated with decol. C. and evaporated to dryness. A solution of the residue in ethyl acetate was eluted through an alumina ethylacetate column. To a suspension of the oil in dry ether was added ethereal HCl. dropwise until the solution was acid. The supernatant liquid was decanted and the solid residue triturated and washed with dry ether to give a white powder. The residue was crystallised from ethanol-ether to give 2-chloro-N-methyl-N-[1-(dimethylamino)-α-methylcyclohexanemethyl]benzamide hydrochloride (0.24 g. 13%), m.p. 214°.

EXAMPLE 30

1-[3,4-Dichlorobenzoylaminomethyl]-N-methyl-N-Benzylcyclohexylamine

A solution of 3,4-dichlorobenzoyl chloride (2.095 g.) in benzene (50 ml) was added to a solution of 1-aminomethyl-N-methyl-N-benzylcyclohexylamine (2.32 g.) in benzene (50 ml) and the mixture heated under reflux for 1 hr. The solution was allowed to cool, washed with 2N sodium hydroxide solution (3 × 50 ml), water (4 × 100 ml), dried ($Na_2SO_4$) and evaporated to give a white crystalline solid (4.0 g). Recrystallisation from cyclohexane afforded 1-[3,4-dichlorobenzoylaminomethyl]-N-methyl-N-benzylcyclohexylamine (110/39) as white prisms (3.589 g. 89%) m.p. 139°–145°.

EXAMPLE 31

1-Aminomethyl-N-methyl-N-benzylcyclohexylamine

A solution of sodium cyanide (5.145 g.) in water (25 ml) was added dropwise to a stirred solution of N-methylbenzylamine hydrochloride (15.75 g.) and cyclohexanone (9.8 g) in water (12 ml) with ice-water cooling. The resulting mixture was stirred overnight, diluted with water and extracted with ether (4 × 200 ml). The ether extracts were washed with water (4 × 500 ml), dried ($Na_2SO_4$) and evaporated to leave an orange oil (20.4 g). The crude oil (10 g.) was dissolved in benzene (10 ml) and chromatographed on a column of silica (50 × 4.4 cms) eluting with benzene/ether 1:1 and fractions (4 × 250 ml) were collected. Fractions (2) and (3) were combined, evaporated and rechromatographed on a column of silica (50 × 4.4 cms) eluting with benzene/ether 4:1. Fractions (8 × 100 ml) were collected. Fractions (3–6) were combined and evaporated to give a colourless oil (7.0 g.). The remaining oil (10.4 g) was purified similarly giving 1-cyano-N-methyl-N-benzylcyclohexylamine (14 g. 61%) as a colourless oil.

1-Cyano-N-methyl-N-benzylcyclohexylamine (57.0 g) in ether (50 ml) was added dropwise to a stirred suspension of lithium aluminium hydride (12.7 g) in ether (500 ml) cooled in an ice-water bath. The mixture was stirred overnight and excess water added dropwise, with ice-water cooling, to destroy the excess lithium aluminium hydride. The mixture was filtered on hyflo, the layers separated and the aqueous layer extracted with ether (3 × 200 ml). The combined ether extracts were washed with water (4 × 200 ml), dried ($Na_2SO_4$) and evaporated to leave a colourless oil (52.6 g). The residual oil was distilled to give 1-Aminomethyl-N-methyl-N-benzylcyclohexylamine b.p. 116°–141° 0.05–0.5 mm.

EXAMPLE 32

N-[1-methyl-N-methyl-N-benzylcyclohexylamine]benzamide and hydrochloride

A solution of benzoyl chloride (2.108 g., 1.73 ml) in dry benzene (75 ml) was added to a solution of 1-aminomethyl-N-methyl-N-benzylcyclohexylamine (3.142 g) in dry benzene (75 ml) and the solution refluxed for one hour. The solution was allowed to cool, washed with 2N sodium hydroxide (2 × 100 ml), water (4 × 200 ml), dried ($Na_2SO_4$) and evaporated yielding a white crystalline solid (5.2 g). Recrystallisation from cyclohexane /40–60 petrol 1:1 afforded N-[1-methyl-N-methyl-N-benzylcyclohexylamine] benzamide as white prisms (4.341 g. 86%) m.p. 118°–124°.

N-[1-methyl-N-methyl-N-benzylcyclohexylamine]benzamide hydrochloride

N-[1-methyl-N-methyl-N-benzylcyclohexylamine] benzamide (0.673 g.) was dissolved in absolute ethanol (5 ml) and ethereal hydrogen chloride (5 ml) was added. The resulting solution was evaporated to give a white semicrystalline solid which was dissolved in the minimum of ethanol. Dropwise addition of ether with scratching and ice-water cooling, precipitated a white crystalline solid which was filtered. Recrystallisation from ethanol (addition of ether) afforded N-[1-methyl-N-methyl-N-benzylcyclohexylamine] benzamide hydrochloride as a white powder (0.895 g. 93%) m.p. 195°–200° C.

EXAMPLE 33

N-[1-methyl-N-methylcyclohexylamine]Benzamide and hydrochloride

N-[1-Methyl-N-methyl-N-benzylcyclohexylamine] benzamide prepared as in Example 32 (3.365 g) was dissolved in acetic acid (50 ml), palladium black (0.200 g) was added, and the atmosphere saturated with hydrogen at atmospheric pressure with vigorous stirring over four hrs. The catalyst was filtered on celite, the filtrates diluted with water and basified with 5N sodium hydroxide solution. The cloudy solution was extracted with ether (4 × 200 ml) the ether extracts washed with water (4 × 200 ml), dried ($Na_2SO_4$) and evaporated to leave a colourless oil (2.4 g). The oil was dissolved in ether (10 ml) and chromatographed on a column of alumina (30 × 3.0 cms) eluting initially with ether (5 × 100 ml fractions) and finally methanol (5 × 100 ml. fractions). Fractions 7–9 were combined and, on evaporation afforded N-[1-methyl-N-methylcyclohexylamine]benzamide as a pale yellow oil (2.253 g. 91%).

N-[1-methyl-N-methylcyclohexylamine]benzamide (0.493 g.) was dissolved in absolute ethanol (2 ml) and ethereal hydrogen chloride (1 ml) was added. The resulting solution was evaporated and the oil dissolved in the minimum of absolute ethanol. Dropwise addition of ether, with scratching, precipitated a white crystalline solid which was filtered. Recrystallisation from absolute ethanol (addition of ether) afforded N-[1-methyl-N-methylcyclohexylamine]benzamide hydrochloride (0.427 g. 75%) as white prisms, m.p. 152°–154°.

EXAMPLE 34

2,6-Dichloro-[1-(Dimethylamine)-cyclohexanemethyl]-benzylamine Dihydrochloride

A solution of 2,6-dichlorobenzylchloride (1.25 g) in dry benzene (15 ml) and a solution of 1-aminomethylcyclohexyldimethylamine (1.0 g.) in dry benzene (15 ml) were mixed and heated on the steam-bath for 1½ hrs. The colourless solution was evaporated to dryness and reevaporated with ethanol to give a basic semi-solid. This was dissolved in water (15 ml), acidified with 2N HCl, and extracted with ether (2 × 25 ml). The ethereal extract was discarded, the aqueous (acid) solution was cooled, made alkaline with 5N HaOH, the basic solution extracted with ether (3 × 100 ml) and dried (anhyd. $Na_2SO_4$). The ethereal extract was evaporated to dryness to give an oil (1.4 g) which was converted to the dihydrochloride (1.9 g) and crystallised from ethanol to give 2,6-dichloro-[1-(dimethyl amino)-cyclohexanemethyl]benzylamine dihydrochloride (0.5 g) m.p. 216° C (dec.)

EXAMPLE 35

1-(1-Aminomethylcyclohexyl) piperidine 1-(1-cyanocyclohexyl) piperidine (1.92 g. 0.01 mole) was dissolved in dry ether (50 ml) and added dropwise to a stirred suspension of LiAlH$_4$ (0.76 g. 0.02 mole) in dry ether (100 ml). The suspension was stirred overnight and worked up as in (1b) to give a colourless oil (1.4 g 74.4%) which on treatment with ethanolic HCl gave colourless needles of 1-(1-aminomethylcyclohexyl) piperidine dihydrochloride m.p. 256°-7°.

The 1-(1-cyanocyclohexyl)piperidine was prepared as follows:

Piperidine hydrochloride (24.1 g 0.2 mole) and KCN (13.0 g. 0.2 mole) were dissolved in water (80 ml) and ethanol (160 ml). To this stirred solution was added dropwise a solution of cyclohexanone (19.6 g., 0.2 mole) in ethanol (40 ml), the mixture refluxed for 24 hr. Ethanol was then removed under reduced pressure and the residue extracted with chloroform. The extract was washed with water, dried (Na$_2$SO$_4$) and evaporated under reduced pressure to give a pale, amber oil (27.0 g. 68.8%) which crystallised on standing. Recrystallisation from ethanol afforded colourless plates of 1-(1-cyanocyclohexyl)piperidine m.p. 67°-8°.

EXAMPLE 36

1-[1-(Formamidomethyl)cyclohexyl]piperidine

Chloral (4.65 g.) was added dropwise to a cooled solution of 1-[1-(aminomethyl)cyclohexyl]piperidine (5.9 g) in dry chloroform (30 ml). The mixture was stirred at room temperature for 16 hrs. and then heated under reflux for 30 mins. The solution was evaporated to dryness and the oily residue re-evaporated with ether. This residual brown oil (7.9 g) was distilled under high vacuum to give a viscous pale yellow oil of 1-[1-(formamidomethyl)cyclohexyl)piperidine (5.1 g.) b.p. 170°-2° C at 1.7 mm.

EXAMPLE 37

1-[1-(Acetamidomethyl)cyclohexyl]piperidine

1-[1-(Aminomethyl)cyclohexyl]piperidine (9.8 g) was added dropwise to ice-cold acetic anhydride (40 ml) with constant stirring. The mixture was stirred for a further 15 mins. and heated under reflux for 1¼ hrs. The solution was evaporated to dryness and reevaporated with ethanol/benzene. This oily residue was dissolved in water (30 ml) and made alkaline with 5N NaOH (top H1O). The solution was extracted with chloroform (3 × 50 ml) and the chloroform extracts were washed with water and dried (anhyd. Na$_2$SO$_4$). The chloroform solution was evaporated to dryness under reduced pressure to give a basic oil (14.8 g.) which was dissolved in petroleum ether (b.p. 60°-80°) and treated with charcoal. The filtered solution was allowed to cool and the solid which separated was crystallised from petroleum ether (b.p. 60°-80°) to give 1-[1-(acetamidomethyl)cyclohexyl]piperidine (7.8 g.) m.p. 104°.

EXAMPLE 38

1-(4-Fluorobenzamidomethylcyclohexyl) piperidine

A mixture of 1-(1-aminomethylcyclohexyl) piperidine (1.5 g.), 4-fluorobenzyl chloride (2 ml) and pyridine (10 ml) was allowed to stand at room temperature for 1 hr. The crystalline material produced was filtered (2.35 g. 86.6%) and afforded pale lemon rosettes of 1-(4-fluorobenzamido-methylcyclohexyl)piperidine, hydrochloride m.p. 243°-5° (Decomp.).

EXAMPLE 39

1-(2-Chlorobenzamidomethylcyclohexyl) piperidine

A mixture of 1-(1-aminomethylcyclohexyl) piperidine (1.5 g.), 2-chlorobenzoyl chloride (2 ml) and pyridine (10 ml) was allowed to stand at room temperature for 1 hr. with no apparent effect. The mixture was therefore refluxed for 1 hr., cooled, diluted with water, basified with ammonia and extracted with chloroform. This chloroform extract was washed with water, dried (Na$_2$SO$_4$), and evaporated to give a viscous, brown oil (3.0 g. 79.2%). On dissolving in ether and bubbling dry HCl gas into the solution pale buff rosettes of 1-(2-chlorobenzamidomethylcyclohexyl) piperidine hydrochloride, m.p. 234°-6° were obtained (from ethanol/ether).

EXAMPLE 40

1-(3,4-Dichlorobenzamidomethylcyclohexyl) piperidine

A mixture of 1-(1-aminomethylcyclohexyl) piperidine (1.5 g.), 3,4-dichlorobenzoyl chloride (2 g.) and pyridine (10 ml) was allowed to stand at room temperature for 1 hr. when the whole mass solidified. Recrystallisation from ethanol/ether several times gave small colourless needles of 1-(3,4-dichlorobenzamidomethylcyclohexyl) piperidine hydrochloride (1.7 g. 54.8%), m.p. 235°-236° (decomp.).

EXAMPLE 41

1-[1-(3,4,5-trimethoxybenzamidomethyl)cyclohexyl]-piperidine hydrochloride

A solution of 3,4,5-trimethoxybenzoylchloride (1.2 g.) and 1-[1-(aminomethyl)cyclo-hexyl]piperidine (1.0 g) in dry benzene (50 ml) was heated under reflux for 1½ hrs. The solid which separated was filtered, washed with benzene and crystallised from isopropanol to give 1-[1-3,4,5-tri-methoxybenzamidomethyl)cyclohexyl]-piperidine hydro-chloride (1.2 g. 58%) m.p. 241° (decomp.).

EXAMPLE 42

[(1-piperidinocyclohexyl)methyl]carbamic acid, ethyl ester

A solution of 1-[1-(aminomethyl)cyclohexyl] piperidine (1.0 g.) in dry benzene (10 ml) and ethyl chloroformate (0.6 g.) in dry benzene (10 ml) was mixed and heated under reflux for 30 mins. The solid which precipitated was filtered, and the residue washed with benzene.

The solid was crystallised from isopropanol to give [(1-piperidinocyclohexylmethyl]carbamic acid, ethyl ester (0.7 g. 45%) m.p. 208° (decomp.).

EXAMPLE 43

1-[1-(p-nitrobenzamidomethyl)cyclohexyl]-piperidine, hydrochloride

Solutions of 1-[1-(Aminomethyl)cyclohexyl]-piperidine (2 g.) in dry benzene (15 ml) and p-nitrobenzoylchloride (1.9 g.) in dry benzene (15 ml) were mixed and heated on a steam bath for 50 mins. The solid which separated on cooling was filtered and crystallised from isopropanol to give a crystalline solid (2.65 g).

The solid was dissolved in hot ethanol, made acid with ethereal HCl and evaporated to dryness. The residue was crystallised from ethanol to give 1-[1-(p-nitrobenzamido methyl)cyclohexyl]-piperidine, hydrochloride (61%) m.p. 254°-256°.

EXAMPLE 44

1-[1-(p-Aminobenzamidomethyl)cyclohexyl]piperidine

A solution of 1-[1-(p-nitrobenzamidomethyl) cyclohexyl]piperidine hydrochloride (2 g.) in water (20 ml) was made alkaline with 5N NaOH and the suspension extracted with chloroform (3 × 30 ml.). The combined chloroform extracts were dried (anhyd. $Na_2SO_4$) and evaporated to give a yellow solid (1.7 g.). To a stirred solution of this in ethanol (100 ml) containing Raney Nickel in suspension was added dropwise a solution of hydrazine hydrate (5 ml) in ethanol (5 ml) over 30 mins. The suspension was stirred for a further 3½ hrs., the suspension was heated to boiling for 30 mins. and filtered through Hyflo. The filtrate was evaporated to dryness and the white solid which formed was crystallised from benzene to give 1-[1-(p-aminobenzamidomethyl) cyclohexyl]piperidine (0.95 g. 50%), m.p. 160°-163°.

EXAMPLE 45

1-(1-Methylaminomethylcyclohexyl) piperidine 1-(1-Formylaminomethylcyclohexyl) piperidine (4.48 g. 0.02 mole) was reduced with $LiAlH_4$ (1.52 g. 0.04 mole) and the suspension worked up as in (Ib) to give an amber, mobile oil (4.1 g. 93.0%) which on treatment with ethanolic HCl gave colourless needles of 1-(1-methylaminomethylcyclohexyl) piperidine dihydrochloride m.p. 259-60°.

EXAMPLE 46

1-[1-Ethylaminomethyl)cyclohexyl]piperidine and its dihydrochloride

A solution of 1-[1-(acetamidomethyl)cyclohexyl] piperidine (5.5 g.) in dry tetrahydrofuran (50 ml) was added dropwise with stirring during 10 mins. to a suspension of lithium aluminium hydride (3.8 g.) in dry tetrahydrofuran (100 ml). The mixture was heated under reflux for 5½ hrs. and stirred at room temperature for 16 hrs. Water (10 ml) was added dropwise to decompose excess lithium aluminium hydride (grey suspension had turned white). The suspension was filtered through hyflo, washed with ether and the combined filtrates dried (anhyd. $Na_2SO_4$). The dried filtrate was evaporated to dryness under reduced pressure and the residual oil (5 g.) was distilled under high vacuum to give 1-[1-(Ethylaminomethyl)cyclohexyl]piperidine (3.5 g.). b.p. C 138°-144° at 5.5 mm.

Dihydrochloride

The base (3.5 g.) was converted to the dihydrochloride (in ether) and was crystallised from ethanol to give 1-[1-(ethylaminomethyl)cyclohexyl]piperidine dihydrochloride (2.1 g.) m.p. 246°-247° dec.

EXAMPLE 47

1-N-Formyl-1-methylaminomethylcyclohexyl) piperidine

Formic acid 98/100% (13.8 g. 0.3 mole) and acetic anhydride (30.6 g. 0.3 mole) were mixed without cooling and kept at room temp. for 1 hr. 1-(1-methylaminomethylcyclohexyl) piperidine (4.2 g. 0.02 mole) was dissolved in formic acid (15 ml) and the formylating agent (25 ml) added slowly. This produced effervescence and a rise in temp. to 60°. The mixture was allowed to stand at room temp. overnight and the solvents then evaporated under reduced pressure to yield a viscous, amber oil (3.79 g. 80%) which crystallised on cooling and gave colourless prisms of 1-(N-formyl-1-methylaminomethylcyclohexyl) piperidine m.p. 94° (from light petroleum b.p. 60°-80°).

EXAMPLE 48

1-(1-Dimethylaminomethylcyclohexyl)piperidine 1-(N-Formyl-1-methylaminomethylcyclohexyl)-piperidine (2.38 g, 0.01 mole) was dissolved in dry ether (50 ml) and added dropwise to a stirred suspension of lithium aluminium hydride (0.76 g, 0.02 mole) in dry ether (100 ml). The suspension was stirred overnight and the product worked up in a similar manner to previous lithium aluminium hydride experiments. Removal of ether gave a colourless, mobile oil (1.59 g, 72.1%) which on treatment with 10% ethanolic hydrochloric acid gave colourless needles of 1-(1-dimethylaminomethylcyclohexyl)-piperidine dihydrochloride, m.p. 224° (from ethanol/ether).

EXAMPLE 49

N-methyl-N-[(1-piperidinocyclohexyl)methyl]acetamide

A mixture of 1-[1-[(methylamino)methyl]cyclohexyl]-piperidine (1.0 g., 0.005 mole) and acetic anhydride (10 ml) was heated on a steam-bath for 30 mins. The solution was evaporated to dryness and water (5 ml) was added to the residue. A saturated solution of sodium carbonate (10 ml) was added and the alkaline solution was extracted with chloroform (50 ml × 3) and dried (anhyd. $Na_2SO_4$). The chloroform solution was evaporated to dryness and the oily residue re-evaporated with ether. This was dissolved in petroleum ether (60°-80° C), treated with decol. charcoal, and filtered (hyflo). The combined filtrates were evaporated to dryness to give N-methyl-N-[(piperidino cyclohexyl)methyl]-acetamide (1.3 g.).

EXAMPLE 50

N-Methyl-N[(1-piperidinocyclohexyl)methyl]3,4-dichlorobenzamide hydrochloride

Solutions of 1-[1-[(methylamino)methyl]cyclohexyl] piperidine (1.1 g., 0.005 mole) in dry benzene (25 ml) and 3,4-dichlorobenzoyl-chloride (1.0 g., 0.005 mole) in dry benzene (50 ml) were mixed and heated under reflux (steam bath) for 1 hr. The precipitate was filtered washed with benzene and dried. (1. 6 g.) m.p. 222° (dec.)

Crystallisation from isopropanol gave N-methyl-N[(1-piperidinocyclohexyl)methyl[3,4-dichlorobenzamide hydrochloride (0.9 g.,) m.p. 239° (dec.)

EXAMPLE 51

1-(1-Aminomethylcyclohexyl)-4-methyl piperazine 1-(1-Cyanocyclohexyl)-4-methylpiperazine (4.1 g, 0.02 mole) was dissolved in dry ether (100 ml) and added dropwise to a stirred suspension of lithium aluminium hydride (1.52 g, 0.04 mole) in dry ether (200 ml.). The suspension was stirred overnight and excess lithium aluminium hydride decomposed by dropwise addition of water (4 ml.), 30% sodium hydroxide solution (3 ml), and water (14 ml). The ether layer was separated, dried ($Na_2SO_4$), and evaporated to yield a colourless mobile oil (3.48 g, 82.9%). An aliquot was refluxed with ethanol (10 ml.) and excess methyl iodide for 0.5 hr. to give yellow needles of 1-(1-methylaminocyclohexyl)-4-methyl piperazine dimethiodide which was recrystallised from methanol/ether as pale yellow needles, m.p. 243°-5°.

EXAMPLE 52

1-(1-Formylaminomethylcyclohexyl)-4-methylpiperazine

Formic acid (6.9 g, 0.15 mole) and acetic anhydride (15.3 g, 0.15 mole) were mixed without cooling and kept at room temperature for 1 hr. 1-(1-aminomethylcyclohexyl)-4-methylpiperazine (8.4 g, 0.04 mole) was dissolved in formic acid (12 ml) and the formylating mixture (16 ml) added. This produced vigorous effervescence and a rise in temperature to 70°. The mixture was left at room temperature for 2 hr. and then heated on a water bath at 55° for 0.75 hr. The solvents were removed under reduced pressure yielding a viscous brown oil (6.0 g, 66.3%) which crystallised as colourless plates of 1-(1-formylaminomethylcyclohexyl)-4-methylpiperazine from light petroleum (b.p. 80°-100°), m.p. 97°-98°.

EXAMPLE 53

1-[1-(Acetamidomethyl)cyclohexyl]-4-methyl piperazine

1-[1-(Aminomethyl)cyclohexyl]-4-methyl piperazine (10.57 g.,) was added slowly to stirred acetic anhydride (40 ml) cooled in ice and the stirring was continued for 15 mins. The mixture was heated under reflux for 1 hr.. The solution was evaporated to dryness and re-evaporated with ethanol/benzene (X2). The residue was dissolved in water the solution made alkaline with 5NNaOH (pH = 14), extracted with chloroform (X3), dried (anhyd.$Na_2SO_4$) and evaporated. The residue was dissolved in hot petroleum ether (80°-100°) decolourised with charcoal and allowed to cool. The crystalline solid which formed was recrystallised from petroleum ether (b.p. 80°-100°) to give 1-[1-(acetamidometyl)cyclohexyl]-4-methyl piperazine (8.3 g; 65%) m.p. 110°-111°.

EXAMPLE 54

1-[1-(3,4 Dichlorobenzamidomethyl)cyclohexyl]-4-methyl-piperazine.

A solution of 3,4-Dichlorobenzoylchloride (1.05 g.,) in benzene (10 ml) was added dropwise over 40 mins. to a stirred solution of 1-[1-)Aminomethyl)cylcohexyl]-4-methyl piperazine (1.06 g.,) in benzene (15 ml). The mixture was heated under reflux for 1 hr. on a steam-bath and the solution was evaporated. The solid residue was dissolved in ethanol, acidified with ethereal HCl and evaporated to give a white solid. This solid was suspended in water made alkaline with 5NNaOH and extracted with chloroform (x2). The combined chloroform extracts were dried (anhyd.$Na_2SO_4$) and evaporated. The solid residue was dissolved in hot petroleum ether (80°-100°) decolourised with charcoal and crystallised from petroleum ether (80°-100°) to give 1-[1-(3,4 Dichlorobenzamido methyl) cyclohexyl]-4-methyl piperazine (0.95 g; 49%) m.p. 143° -146°.

EXAMPLE 55

1-[1-(3,4,5-Trimethoxybenzamidomethyl)cyclohexyl]-4-methyl piperazine hydrochloride A solution of 3,4,5-trimethoxybenzoyl chloride (2.2 g;) in dry benzene (25 ml) and a solution of 1-[1-(aminomethyl)cyclohexyl]-4-methyl piperazine (0.2g;) in dry benzene (25 ml) were mixed and heated under reflux for 1 hr. The solid which formed was filtered, washed with benzene and was crystallised from isopropanol-ether to give 1-[1-(3,4,5-trimethoxybenzamidomethyl)cyclohexyl]-4-methyl piperazine hydrochloride (1.9 g., 45.4%) m.p. 208°-9° C.

EXAMPLE 56

1-(1-Tosylaminomethylcyclohexyl)-4-methylpiperazine 1-(1-Aminomethylcyclohexyl)-4-methylpiperazine (0.5 g) was added to 10% sodium hydroxide solution (10 ml) and p-toluene sulphonyl chloride (0.5 g), and the mixture shaken vigorously. The solid was filtered, washed with water and recrystallised from 95% ethanol to give colourless needles (0.4 g, 46.2%) of 1-(1-tosylaminomethylcyclohexyl)-4-methyl piperazine, m.p. 128°-130°.

EXAMPLE 57

1-(1-Methylaminomethylcyclohexyl)-4-methylpiperazine 1-(1-Formylaminomethylcyclohexyl)-4-methylpiperazine (5.97 g, 0.025 mole) was dissolved in dry benzene (100 ml) and added dropwise to a stirred suspension of lithium aluminum hydride (3.8 g; 0.1 mole) in dry ether (200 ml). The suspension was refluxed for four days and excess lithium aluminium hydride decomposed by the dropwise addition of water (8 ml), 30% sodium hydroxide solution (6 ml) and water (28 ml). The ether/benzene layer was separated, dried ($Na_2SO_4$) and evaporated to yield an amber, mobile oil (5.2 g. 93.0%) which failed to crystallise or produce stable salts. Distillation of this oil in vacuo gave 1-(1-methylaminomethylcyclohexyl)-4-methylpiperazine as a colourless oil.

EXAMPLE 58

1-[1-(Ethylaminometyl)cyclohexyl]-4-methyl piperazine and dihydrochloride

1-[1-(Ethylaminomethyl)cyclohexyl]-4-methyl piperazine (2)

To a stirred solution of lithium aluminum hydride (3 g.,) in dry tetrahydrofuran (40 ml) was added a solution of 1-[1-(Acetamidomethyl)cyclohexyl]-4-methyl piperazine (3 g.,) in dry tetrahydrofuran (40 ml) dropwise. The stirring was continued overnight, the suspension was heated under reflux for a further 6 hrs. and the excess $LiAlH_4$ neutralised with water. The mixture was filtered and the filtrate was dried (anhyd. $Na_2SO_4$) and evaporated to an oil, which was micro distilled to give 1-[1-(Ethylaminoemthyl)-cyclohexyl]-4-methyl piperazine as a colourless oil.

b.p. 35mm 105°-109° (1.96 g., 69%).

1-[1-Ethylaminomethyl)cyclohexyl]-4-methyl piperazine dihydrochloride (3)

To a solution of 1-[1-(Ethylaminomethyl)cyclohexyl]-4-methyl piperazine (1.5 g.,) in ether (20 ml) was added excess of ethereal HCl. The suspension was evaporated to dryness and the residual oil was re-evaporated with ethanol/ether (x2). The residue was dissolved in a minimum amount of hot ethanol, the solution was cooled and excess isopropanol was added. The solid which separated was filtered and crystallised from ethanol/isopropanol to give 1-[1-(Ethylaminomethyl)-cyclohexyl]-4-methyl piperazine, dihydrochloride (0.15 g.) m.p. 231°–234°.

EXAMPLE 59

1-(1-Methyl formylaminomethyl-1-cyclohexyl)-4-methyl piperazine

Formic acid (3.45 g, 0.07 mole) and acetic anhydride (7.65 g, 0.07 mole) were mixed without cooling and kept at room temperature for 1 hr. 1-(1-Methylaminomethyl-1-cyclohexyl)-4-methylpiperazine (2.25 g, 0.01 mole) was dissolved in formic acid (6 ml) and the formylating mixture (8 ml) added. This produced vigorous effervescence and a temperature rise to 60°. The mixture was left at room temperature for 2 hr. and then heated on a water bath at 55° for 0.75 hr. The solvents were removed under reduced pressure to give a viscous reddish-brown oil (2.13 g, 83.3%) which crystallised as colourless needles of 1-(1-Methylformylaminomethyl-1-cyclohexyl)-4-methylpiperazine from light petroleum (b.p. 80°–100°), m.p. 107°–108°.

EXAMPLE 60

3,4-Dichloro-N-methyl-N-[[1-(4-methyl-1-piperazinyl) cyclohexyl]methyl]benzamide A solution of 3,4-dichlorobenzoylchloride (0.61 g.,) in benzene (10 ml) was added dropwise over 25 mins. to a stirred solution of 1-[1-(methylaminomethyl)cylcohexyl]-4-methyl piperazine (1) (0.65 g.). The mixture was then heated on a steambath for 1 hr. and the mixture was evaporated to dryness. The residue was dissolved in hot light petroleum (60°–80°) and decolourised with charcoal. The solid which separated was crystallised from light petroluem (60°–80°) to give 3,4-Dichloro-N-methyl-N-[[1-(4-methyl-1-piperazinyl)cyclohexyl]methyl]benzamide (0.27 g., 23%) m.p. 126°–129°.

EXAMPLE 61

1-(1,1-Dimethylaminomethyl-1-cyclohexyl)-4-methyl-piperazine 1-(1-Methylformylaminomethyl-1-cyclohexyl)-4-methyl piperazine (0.76 g, 0.003 mole) was dissolved in dry ether (40 ml) and added dropwise to a stirred suspension of lithium aluminium hydride (0.23 g, 0.006 mole) in dry ether (100 ml). The suspension was refluxed for 48 hr. and excess lithium aluminium hydride decomposed by dropwise addition of water (0.4 ml), 50% sodium hydroxide solution (0.3 ml) and water (1.4 ml). The ether layer was separated, dried ($Na_2SO_4$) and evaporated to yield a colourless mobile oil (0.47 g, 72.2%) which failed to crystallise. Treatment with ethanol/methyl iodide gave colourless prisms of 1-(1,1,1-trimetylaminomethyl-1-cyclohexyl)-4,4-dimethylpiperazinium dioxide m.p. 171°–172°.

EXAPLE 62

1-(1-1′-Aminobenzylcyclohexyl)-4-methylpiperazine 1-(1-Benzylimidoylcyclohexyl)-4-methylpiperazine (5.7 g, 0.02 mole) was dissolved in dry ether (150 ml) and the solution added dropwise to a stirred suspension of lithium aluminium hydride (1.52 g, 0.04 mole) in dry ether (150 ml). The suspension was stirred overnight and excess lithium aluminium hydride decomposed by dropwise addition of water (4 ml), 30% sodium hydroxide solution (3 ml) and water (14 ml). The ether layer was separated, dried ($Na_2SO_4$), and evaporated to yield an amber, mobile oil (5.02 g, 87.6%) which solidified on cooling. The solid was recrystallised from acetone/water to give colourless needles of 1-(1,1′-aminobenzylcyclohexyl)-4-methylpiperazine, m.p. 182° (decomp).

EXAMPLE 63

2-Dimethylamino-2-methyl-propionamide

Conc. Sulphuric acid (8 ml.) was added to 2-dimethylamino-2-methyl-propionitrile (2 g.), and was heated to 90° C and allowed to stand for five mins. The reaction mixture was added to ice cold water (100 ml.), barium hydroxide (32 g.) was added to neutralise the acid and the mixture was filtered (hyflo). The filtrate was evaporated under reduced pressure to give a solid residue which was crystallised from light petroleum (80°–100° C) to give 2-dimethylamino-2-methylpropionamide (1 g. 45%) m.p. 109°–111° C.

EXAMPLE 64

2-Dimethylamino-2-methyl-propylamine-dihydrochloride

A solution of 2-dimethylamino-Lb 2-methyl propionamide (2.5 g.) in tetrahydrofuran (50 ml.) was added to a cooled, stirred suspension of lithium aluminium hydride (0.8 g.) in tetrahydrofuran (100 ml.). The mixture was refluxed for 16 hrs. and then water was added to decompose the excess lithium aluminium hydride. The mixture was dried (anhyd. sodium sulphate) and extracted with ether. The ether extracts were extracted with 2N hydrochloride acid (3 × 15 ml.) and the excess water evaporated under reduced pressure to give a solid residue which was crystallised from methanol to give 2-dimethylamino-2-methyl-propylamine-dihydrochloride (2 g. 56%) m.p. 254°–256° C.

EXAMPLE 65

3,4-Dichloro-N-[2-dimethylamino-2-methyl-propyl]-benzamide hydrochloride monohydrate 2-Dimethylamino-2-methyl-propylamine-dihydrochloride (1.65 g.) was dissolved in water (2 ml.) and made alkaline (5N NaOH). Benzene (150 ml.) was added and the mixture dried (anhyd. sodium sulphate). The suspension was filtered, and the benzene solution added to a solution of 3,4-dichlorobenzoyl chloride (1.8 g.) in benzene (50 ml). The mixture was refluxed for 45 mins. and the solid which separated was crystallised from methanol/isopropanol to give 3,4-dichloro-N-[2-dimethylamino-2-methyl-propyl]-benzamide hydrochloride monohydrate (1.6 g. 59%) m.p. 192°–194° C.

EXAMPLE 66

3,4-Dichloro-N-[1,2-Dimethyl-2-(dimethylamino)-propyl]-benzamide hydrochloride.

2-Dimethylamino-1,2-dimethyl-propylamine dihydrochloride.

A solution of methyl iodide (15.5 g.) in ether (50 ml.) was added dropwise to a stirred suspension of lithium turnings (1.9 g.) in ether (100 ml.) at −10° C. in an atmosphere of nitrogen. The mixture was stirred for one hour whilst the temperature rose frm −10° C to 10° C. The methyl lithium was filtered under nitrogen and a solution of 2-(dimethylamino)-2-methyl propionitrile (10 g.) in ether (50 ml.) added dropwise to the cooled methyl lithium solution. The solution was stirred overnight and water (15 ml.), added to decompose the inorganic complexes. The mixture was dried (anhydrous sodium sulphate), extracted with ether and the ether was distilled to give imine (10 g.).

A solution of the imine in ether was added dropwise to a stirred and cooled suspension of lithium aluminum hydride (5.9 g.) in ether (100 ml.). The mixture was heated under reflux overnight and the excess lithium aluminium hydride was decomposed with water (5 ml.). The suspension was dried over anhydrous sodium sulphate and filtered. The ethereal solution was extracted with 2N hydrochloric acid (3 × 15 ml.) and the acid extract was evaporated under reduced pressure to give a solid residue which was crystallised from ethanol/methanol to give 2-dimethylamino-1,2-dimethylpropylamine dihydrochloride (8.5 g.) m.p. 252°–4°.

EXAMPLE 67

3,4-Dichloro-N-[1,2-dimethyl-2-dimethylamino-propyl]-benzamide hydrochloride

2-Dimethylamino-1,2-dimethyl-propylamine dihydrochloride (1.6 g.) was dissolved in 5N sodium hydroxide (5 ml.). Benzene (50 ml.) and anhydrous sodium sulphate was added and the mixture was filtered (hyflo). The combined filtrates were added to a solution of 3,4-dichlorobenzoylchloride (1.6 g.) in benzene (30 ml.) and the mixture was refluxed for 45 mins. on a steam bath. The precipitate which formed was filtered (2.0 g., m.p. 248°–250° C) and crystallised from methanol to give 3,4-dichloro-N-[1,2-dimethyl-2-dimethylamino-propyl]benzamide hyrochloride (1.34 g.) m.p. 252°–4° C.

EXAMPLE 68

O-Chloro-N-[1,2-dimethyl-2-(dimethylamino)-propyl]-benzamide hydrochloride

2-Dimethylamino-1,2-dimethylpropylamine dihydrochloride (1.5 g.) was dissolved in water (3 ml.) and made alkaline with 5N sodium hydroxide. Benzene (100 ml.) was added and the mixture dried (anhyd. Na$_2$SO$_4$) and filtered. The benzene solution was added to a solution of O-chloro-benzoyl chloride (1.3 g.) in benzene (50 ml.), the mixture refluxed for 1.5 hrs. and allowed to stand overnight. The crystals were filtered and recrystallised from isopropanol to give O-chloro-N-[1,2-dimethyl-2-(dimethylamino)-propyl] benzamide hydrochloride (1.9 g.) m.p. 245°–47° C.

EXAMPLE 69

N-[1,2-Dimethyl-2-(dimethylamino)propyl]carbamic acid ethyl ester hydrochloride

2-Dimethylamino-1,2-dimethylpropylamine dihydrochloride (2 g.) was dissolved in water (3 ml.) and made alkaline with 5N NaOH. Benzene (100 ml.) was added and the mixture dried (anhyd. Na$_2$SO$_4$).

A solution of ethyl chloroformate (1.07 g.) in benzene (30 ml.) was added dropwise to the benzene solution and the mixture refluxed for 4 hrs. and allowed to stand overnight. Crystals formed which were filtered to give N-[1,2-Dimethyl-2-(dimethylamino)propyl]carbamic acid ethyl ester hydrochloride (1.5 g.) m.p. 144°–46° C.

EXAMPLE 70

N-methyl-2-dimethylamino-2-methyl propylamine dihydrochloride

2-Dimethylamino-2-methyl-propylamino dihydrochloride (2 g.) was dissolved in water (2 ml.) and the solution made alkaline with 5N sodium hydroxide. Chloroform (100 ml.) was added and the mixture was dried (anhyd. Na$_2$SO$_4$) and filtered. A solution of chloral (1.45 g.) in chloroform (50 ml.) was added to the stirred and cooled chloroform solution. The mixture was heated under reflux for 40 hrs., and the excess chloroform evaporated under reduced pressure to give an oily residue (0.9 g.). This was dissolved in ether (50ml.), the solution was added dropwise to a cooled and stirred suspension of lithium aluminium hydride (0.43 g.) in ether (100 ml) and the mixture was heated under reflux for 16 hrs. On cooling, the excess lithium aluminium hydride was decomposed by the addition of water, and the mixture dried (anhydrous Na$_2$SO$_4$), and extracted with ether. The ether extracts were extracted with 2N NCl (2 × 20 ml. and 40 ml.), the excess water was evaporated under reduced pressure and the liquid residue dried by re-evaporation with ethanol/benzene mixture to give a solid residue. This was crystallised from ethanol to give N-methyl-2-dimethylamino-2-methyl propylamine dihydrochloride (0.9 g.)

EXAMPLE 71

3,4-Dichloro-N-[2-(dimethylamino)-2-methylpropyl]-N-methyl benzamide hydrochloride N-methyl-2-dimethylamino-2-methyl-propylamine dihydrochloride (0.5 g.) was dissolved in water (2 ml.) and the solution was made alkaline with 5N sodium hyroxide. Benzene (100 ml.) was added and the mixture dried (anhyd. Na$_2$SO$_4$), filtered, and added to a solution of 3,4-dichloro-benzoyl chloride (0.5 g.) in benzene (50 ml.). The mixture was heated under reflux for one hour, and the solid which separated was filtered and washed with benzene to give 3,4-dichloro-N-[2-(dimethylamino)-2-methylpropyl]-N-methyl benzamide hydrochloride (0.95 g.) m.p. 163°–165° C.

EXAMPLE 72

2-Benzylmethylamino-2-methyl-propylamine (a) 2-Benzylmethylamino-2-methyl-propionitrile A solution of sodium cyanide (9.8 g.) in water (50 ml.) was added dropwise to a stirred mixture of N-benzylmethylamine hydrochloride (30 g.) in water (100 ml.) and acetone (11 g.), cooled to 0° C. The mixture was stirred for 20 hrs. extracted with ether (4 × 100 ml.) the ether extracts washed with water (1 × 100 ml.) dried (anhyd. Na$_2$SO$_4$) and filtered (hyflo). The excess ether was removed under reduced pressure to give a solid residue (28 g.).

The solid was purified by column chromatography (Silica column with ethyl acetate as eluent) to give 2-benzylmethylamino-2-methyl-propionitrile (18 g.)

(b) 2-Benzylmethylamino-2-methyl-propylamine

A solution of 2-benzylmethylamino-2-methylpropionitrile (6.7 g.) in ether (100 ml.) was added dropwise to a stirred solution of sodium dihydro bis[2-methoxyethoxy] aluminate (28.5 g.) in ether (150 ml.), kept at 0° C. The mixture was then gently refluxed for 20 hrs, and then excess reducing agent was decomposed by the dropwise addition of water to the cooled suspension. The mixture was dried (anhyd.Na$_2$SO$_4$), filtered (hyflo) and the excess ether evaporated under reduced pressure. The residual liquid was distilled under water pump vacuum to give 2-benzylmethylamino-2-methylpropylamine (3.8 g.) b.p. 138°–140° C.

EXAMPLE 73

3,4-Dichloro-N[2-benzylmethylamino-2-methyl-propyl]benzamide hydrochloride

A solution of 2-benzylmethyl-amino-2-methyl-propylamine (0.5 g.) in benzene (25 ml) was added dropwise to a solution of 3,4-dichlorobenzoyl chloride (0.54 g.) in benzene (25 ml.) and the mixture was heated on a steam bath for two hours. On cooling a precipitate appeared which was filtered and recrystallised from ethanol to give 3,4-dichloro-N-[2-benzylmethylamino-2-methylpropyl]benzamide hydrochloride (0.7 g) m.p. 192°–193°.

EXAMPLE 74

2-[N-benzylmethylamino]-1,2-dimethyl propylamine

Methyl iodide (21.3 g.,) in ether (25 ml.) was added dropwise to a suspension of lithium (2.1 g.,) in ether (200 ml.) kept at −10° C and under an atmosphere of N$_2$. When all the lithium had dissolved a solution 2-N-benzylamino-2-methylpropionitrile (9.4 g.,) in ether (50 ml.) was added dropwise to the stirred methyl lithium solution at − 10° C. The mixture was allowed to stir for 20 hrs. The excess methyl lithium was decomposed by the dropwise addition of water to the ice cold mixture. The mixture was dried (anhyd. Na$_2$SO$_4$), filtered (hyflo) and the dry ethereal imine solution added dropwise to an ice cooled, stirred suspension of lithium aluminum hydride (10 g.) in ether (200 ml.). The mixture was gently refluxed for 16 hrs.

The excess LiAlH$_4$ was decomposed by the dropwise addition of water to the ice-cold mixture. The mixture was dried (anhyd. Na$_2$SO$_4$), filtered (hyflo) and the excess ether evaporated under reduced pressure to give a residue liquid. This was distilled under water pump vacuum to give 2[N-benzylmethylamino]-1,2-dimethyl propylamine (4.1 g.) b.p. 151° C.

EXAMPLE 75

3,4-Dichloro-N[2-Benzylmethylamino-1,2-dimethyl propyl] benzamide hydrochloride

A solution of 2[N-benzylmethylamino]-1,2-dimethylpropylamine (0.5 g., 0.0024 mole) in benzene (25 ml.) was added dropwise to a solution of 3,4-dichlorobenzoylchloride (0.51 g., 0.0024 mole) in benzene (25 ml.). The mixture was gently refluxed for 2 hrs. and the benzene evaporated under reduced pressure to give a residual solid. This was recrystallised from isopropanol/ether to give 3,4-dichloro-N-[2-N-benzylmethylamino-1,2-dimethyl propyl]benzamide hydrochloride (0.8 g.)

EXAMPLE 76

N-[2-Benzylmethylamino-2-methyl propyl] benzamide

A solution of 2-benzylmethylamino-2-methyl propylamine (4.0 g.,) in benzene (25 ml.) was added dropwise to a solution of benzoyl chloride (2. 8 g.,) in benzene (25 ml.). The mixture was refluxed on a steam bath for 3 hrs. The excess benzene was evaporated under reduced pressure to give a semi solid residue which was dissolved in water, make alkaline with 5N sodium hydroxide and extracted with ether (3 × 50 ml.). The ether extracts were dried (anhyd. Na$_2$SO$_4$) filtered (hyflo), and the excess ether evaporated under reduced pressure to give a solid residue which was recrystallised from cyclohexane to give N-[2-Benzylmethyl amino-2-methyl propyl]benzamide (4 g.).

EXAMPLE 77

N-[2-Methylamino-2-methylpropyl]benzamide

N-[2-benzylmethylamino-2-methylpropyl]benzamide (3.55 g.,) was dissolved in glacial acetic acid (30 ml.) and hydrogenated over palladium chloride (140 mg.) 320 ml of H$_2$ was taken up. The catalyst was filtered and the filtrate washed with ether (2 × 100 ml.). The filtrate was then made alkaline with 5N sodium hydroxide and extracted with ether (3 × 60 cm$^3$). The ether extracts were dried (anhyd. Na$_2$SO$_4$), filtered and the excess ether evaporated under reduced pressure to give a liquid residue (2.7 g.) the liquid was dissolved in ether (30 ml.). to this was added ethereal HCl in a dropwise manner. The excess ether was evaporated under reduced pressure to give a sticky solid which was refluxed with ethyl acetate for two hours. On cooling crystals of N-[2-methylamino-2-methylpropyl]benzamide hydrochloride were obtained in 70% yield.

EXAMPLE 78

2-Allylmethylamino-2-methylpropylamine (a) 2-Methylamino-2-methylpropionitrile

A solution of sodium cyanide (51.5 g.,) in water (150 ml.) was added dropwise over a period of 1 hr. to a cooled mixture of methylamine hydrochloride (67.5 g.,) acetone (58 g.,) and water (150 ml). The mixture was stirred overnight at room temperature and then made alkaline to litmus by the addition of dilute sodium hydroxide solution and extracted with ether (3 × 100 ml.). The ether extract was washed with water (2 × 50 ml.) dried (MgSO$_4$) and the solvent was removed in vacuo to give a colourless liquid (71.6 g.). This was distilled at 54°–7°/22 mm to give 2-methylamino-2-methylpropionitrile as a colourless liquid (65.8 g., 67%)

(b) A mixture of 2-methylamino-2-methylpropionitrile (14.7 g., 0.15 mole) allyl bromide (18.0g., 0.15 mole), sodium carbonate (15.9 g., 0.15 mole), sodium iodide (0.2 g., 0.001 mole) and methyl ethyl ketone (200 ml.) was heated under reflux for 40 hrs. The sodium carbonate was filtered off and the solvent was removed from the filtrate in vacuo to give a yellow oil, T.L.C. (Silica, ether), three components RF 0.8, 0.4 and 0.0. The oil was passed through a column of silica 40 × 3.5 cm. using ether as an eluent to give 2-allylmethylamino-2-methylpropionitrile (10.0 g., 48%)

(c) 2-Allylmethylamino-2-methylpropionitrile (1.3 g.) in benzene (20 ml., dry) was added dropwise to a stirred solution of sodium dihydro-bis [2-methoxyethoxy]aluminate (6.7 g.,) in benzene (30 ml., dry) under an atmosphere of nitrogen and stirred overnight. The excess reducing agent was decompassed by the dropwise addition of water. The phases were separated, the organic phase was washed with water, the aqueous phase was washed with benzene and the combined organic extract was dried (MgSO$_4$) and the solvent was removed in vacuo to give a pale yellow liquid (1.8 g.). Distillation at 80°–90°/15 mm. gave 2-allylmethylamino-2-methylpropylamine as a colourless liquid (0.8 g., 60%).

EXAMPLE 79

3,4-Dichloro-N-(2-allylmethylamino-2-methylpropyl)-benzamide

A mixture of 2-allylmethylamino-2-methylpropylamine (1.3 g.,) and 3,4-dichlorobenzoyl chloride (3.15 g.,) was heated under reflux in dry benzene (150 ml.) for 1 hrs. The cooled mixture was washed with dilute sodium hydroxide solution (2 × 30 ml.), water (2 × 30 ml.), dried (MgSO$_4$) and the solvent was removed in vacuo to give a yellow oil (3.9 g.). The oil was passed through a column of alumina 40 × 2.5 cm. using ethyl acetate as an eluent to give 3,4-dichloro-N-(2-allylmethylamino-2-methylpropyl)-benzamide as a pale yellow liquid (2.25 g., 71%).

EXAMPLE 80

N-[2-Methyl-2-[methyl(2-propynal)amino]propyl]benzamide

A solution of N-[2-methylamino-2-methylpropyl] benzamide (1 g., 0.0053 mole) in methyl ethyl ketone (25 ml.) was added dropwise to a mixture of propargyl bromide (0.58 g., 0.052 mole), sodium carbonate (0.55 g., 0.0052 mole) and a few crystals of sodium iodide in methylethyl ketone (30 ml.). The mixture was heated gently under reflux for 24 hrs.

The inorganic solids were filtered off and the excess MEK evaporated under reduced pressure to give a liquid residue with traces of solid. Water was added to the residue, the mixture made alkaline with 5N sodium hydroxide and extracted with ether (3 × 50 ml.). The ether extracts were dried (anhyd. Na$_2$SO$_4$), filtered (hyflo) and the excess ether evaporated at atmospheric pressure to give a liquid residue. The residue was loaded onto an alumima column (30 × 3.5 cm.) and eluted with ethyl acetate. Fractions of 25 ml. were collected once t.l.c. spotting had determined that the first of the compounds was leaving the column. Fractions 1 to 7 were combined and the excess ethyl acetate evaporated under reduced pressure to give N-[2-methyl-2-[methyl(2-propynal)amino]propyl]benzamide (1.0 g.)

EXAMPLE 81

N-[2-methyl-2-[methyl(3-methyl-2-butenyl)amino]propyl] benzamide

A solution of N[2-methylamino-2-methylpropyl] benzamide (1 g., 0.0052 mole) in methylethyl ketone (MEK) (25 ml.) was added to a solution of 1-bromo-3-methyl-but-2-ene (0.78 g., 0.0052 mole) in MEK (40 ml.) containing sodium carbonate (0.55 g., 0.0052 mole) and a few crystals of sodium iodide. The mixture was heated under reflux for 30 hrs. The inorganic solids were filtered off and the filtrant concentrated by evaporation under reduced pressure to give a liquid residue. This was loaded onto an alumina column and eluted with ethyl acetate. Fractions (25 mls) were collected and concentrated to give N[2-methyl-2]methyl(3-methyl-2-butenyl)amino]propyl]benzamide (1.2 g.).

The oxalate was prepared as follows:

A solution of anhyd. oxalic acid (0.26 g. mole) in ethyl acetate (20 ml.) was added dropwise to a solution of the base (0.8 g., 0.0029 mole) in ethyl acetate (20 ml.). A sticky ppt. was thrown out. A little methanol was added to the hot mixture to dissolve the ppt. on cooling this gave crystals of N-[2-methyl-2]-(3-methyl-2-butenyl)amino]propyl]benzamide oxalate m.p. (134°–136° C).

EXAMPLE 82

N-[2-[(cyclopropylmethyl)methylamino]-2-methylpropyl]benzamide

A solution of N-[2-methylamino-2-methyl propyl]-benzamide (1 g., 0.0052 mole) in MEK (50 ml.) was added to a solution of cyclopropyl carbinol bromide (0.66 g.,) in MEK (30 ml.) containing sodium carbonate (0.55 g.,) and a few crystals of sodium iodide. The mixture was refluxed for 24 hrs. and then filtered and the excess MEK evaporated under reduced pressure to give a liquid residue. This was passed down an alumina column, eluting with ethyl acetate to give N-[2-[(cyclopropylmethyl)-methylamino]-2-methylpropyl]benzamide (0.9 g.)

A solution of oxalic acid (0.31 g.,) in ethyl acetate was added dropwise to the base (0.9 g.,) in ethyl acetate to give a sticky precipitate. A few drops of methanol were added to the hot mixture to dissolve the ppt. On cooling crystals of N-[2-[(cyclopropylmethyl)methylamino]-2-methyl propyl]benzamide oxalate were obtained. m.p. (142°–144°).

EXAMPLE 83

N-[2-(allylmethylamino)-2-methylpropyl]benzamide oxalate

A solution of N-[2-methylamino-2-methylpropyl]benzamide (1. g.,) in MEK (25 ml.) was added to a solution of allyl bromide (0.58 g.,) in MEK (25 ml.) containing sodium carbonate (0.55 g.,) and a few crystals of sodium iodide. The mixture was refluxed for 24 hrs. The inorganic solids were filtered off and the filtrant concentrated by evaporation under reduced pressure. The liquid residue was eluted down an alumina column with ethyl acetate to give N-[2-(allylmethylamino)-2-methylpropyl]benzamide 1.1 g.

A solution of oxalic acid (0.4 g., 0.0045 mole) in ethyl acetate (20 ml.) was added dropwise to a solution of the base (1 g., 0.0045 mole) in ethyl acetate (20 ml.) to give a sticky precipitate. A few drops of methanol were added to the hot mixture to dissolve the precipitate, on cooling crystals of N-[2-(allylmethylamino)-2-methylpropyl]benzamide oxalate were obtained m.p. (137°–139° C).

EXAMPLE 84

N-[2-methyl-2-(methylphenethylamino)propyl]benzamide

A solution of N-[2-methylamino-2-methylpropyl]benzamide (1 g.,) in methyl ethyl ketone (25 ml) was added dropwise to a mixture of 2-phenylethyl bromide (0.97 g.,) in methyl ethyl ketone (25 ml), sodium carbonate (0.55 g.) and a few crystals of sodium iodide. The mixture was refluxed for 30 hrs.

The inorganic solids were filtered off and the filtrant evaporated under reduced pressure to give an oily residue. This was loaded onto an alumina column and eluted with ethyl acetate. Fractions (15 ml.) were collected and the first 7 fractions were combined and the excess ethyl acetate evaporated under reduced pressure to give N-[2-methyl-2-(methylphenethylamino)propyl]-benzamide (0.5 g.).

N-[2-methyl-2-(methylphenethylamino)propyl]benzamide oxalate

The base (0.4 g.,) was dissolved in ethyl acetate (20 ml) and to it was added dropwise a solution of oxalic acid (0.12 g.) in ethyl acetate (10 ml). A sticky precipitate was thrown out which was crystallised from ethyl acetate/methanol to give N-[2-methyl-2-(methylphenethylamino)propyl]benamide oxalate (0.25 g.) m.p. (150°–152° C).

EXAMPLE 85

2-Methyl-2-Dimethylamino-Hexylamine (a) 2-Methyl-2-dimethylamino-hexanenitrile

A solution of potassium cyanide (34.20 g.,) in water (75 ml.) was added dropwise to a stirred solution of dimethylamine hydrochloride (40.8 g.,) and hexane-2-one (50 g., 0.5 mole) in water (60 ml.) cooled in an ice-water bath. The mixture was vigorously stirred for 24 hrs., diluted with water (200 ml.) and extracted with ether (4 × 200 ml.). The combined ether extracts were washed with water (4 × 200 ml.), dried ($Na_2SO_4$) and evaporated to leave a colourless oil which was distilled at 12 mm. to give a colourless oil which when distilled gave 2-methyl-2-dimethylamino-hexanenitrile as a colourless oil (51.547 g., 67%, b.p. 92°/12 mm).

(b) A solution of 2-methyl-2-dimethylamino-hexanenitrile (7.70 g.,) in dry ether (100 ml.) was added dropwise to a stirred solution of sodium dihydro-bis(2-methoxyethoxy)aluminate (45.3 g., 70% solution in benzene, 25% excess) in dry ether (100 ml.) under nitrogen with ice water cooling. The solution was refluxed overnight under nitrogen and allowed to cool. Ether (200 ml.) was added, followed by dropwise addition of excess water with ice-water cooling to destroy excess reducing reagent. The mixture was filtered on hyflo and the filtrates extracted with ether (4 × 100 ml.). The combined ether extracts were washed with water (4 × 200 ml.), dried ($Na_2SO_4$) and evaporated leaving a colourless oil. Distillation of the oil afforded 2-methyl-2-dimethylamino-hexylamine as a colourless liquid (4.808 g., 61%) b.p. 86–88/12 mm.

EXAMPLE 86

3,4-Dichloro-N-[2-methyl-2-dimethylamino-hexyl]benzamide

A solution of 3,4-dichlorobenzoyl chloride (2.1 g.,) in dry benzene (25 ml.) was added to a solution of 2-methyl-2-dimethylamino-hexylamine (1.58 g.,) in dry benzene (25 ml.) and the mixture heated under reflux for 1.5 hrs. The mixture was diluted with water, basified with 2N sodium hydroxide solution, and extracted with benzene (4 × 100 ml.). The combined benzene extracts were washed with water (4 × 50 ml.), dried ($Na_2SO_4$) and evaporated affording 3,4-dichloro-N-[2-methyl-2-dimethylamino-hexyl]benzamide as a colourless oil (3.6 g., ca 100%) which slowly crystallised.

EXAMPLE 87

N-[2-Methyl-2-Dimethylamino-hexyl]Formamide

To a solution of acetic formic anhydride (2.9 mls., 20 mmole) (prepared by stirring acetic anhydride [2.04 ml.] and formic acid [0.86 ml.] on a water bath at 50°–60° for two hrs. and cooling), was added dropwise, with stirring, 2-methyl-2-dimethylamino-hexylamine (2.37 g.,) at such a rate that the temperature never rose above 40° C. The solution was stirred for 30 mins. ether (6 ml) was added, and stirring continued at room temperature overnight. The mixture was diluted with ether (50 ml.), basified with 2N sodium hydroxide solution and extracted with ether (4 × 100 ml.). Evaporation of the washed (2 × 100 ml.), dried ($Na_2SO_4$) extracts gave a colourless oil (2.2 g.). T.L.C. (silica, methanol) showed two spots: RF 0.5 and RF 0.0. The oil was chromatographed on a column of silica (20 × 3.0 cm.) eluting with methanol and fractions (6 × 100 ml.) were collected. Fractions 2–5 were combined and evaporated affording N-[2-methyl-2-dimethylamino-hexyl]formamide as a colourless oil (1.427 g., 51%).

EXAMPLE 88

N-Methyl-2-methyl-2-dimethylamino-hexylamine

A solution of N-[2-methyl-2-dimethylamino-hexyl]-formamide (1,395 g., 7.5 mmole) in dry tetrahydrofuran (25 ml.) was added dropwise with stirring to an ice-cold suspension of lithium aluminium hydride (0.51 g.,) in dry tetrahydrofuran (25 ml.). After addition, the mixture was heated under refining overnight and allowed to cool. Water was added dropwise, with ice-water cooling, to decompose excess reducing agent. The mixture was filtered on hyflo, the filtrates washed with 2N sodium hydroxide solution (2 × 50 ml.), water (4 × 100 ml.), dried ($Na_2SO_4$) and evaporated to give a pale yellow oil.

The oil was dissolved in benene and extracted with 2N hydrochloric acid (4 × 50 ml.). The acid extracts were basified with 5N sodium hydroxide and extracted with ether (4 × 100 ml.). The ether extracts were washed with water (4 × 100 ml.) dried ($Na_2SO_4$), and evaporated affording N-methyl-2-methyl-2-dimethylamino-hexylamine as a pale yellow oil (0.800 g., 62%)

EXAMPLE 89

3,4-Dichloro-N-methyl-N-[2-methyl-2-dimethylamino-hexyl]benzamide

A solution of 3,4-dichlorobenzoyl chloride (1.048 g., 5 mmole) in dry benzene (25 ml.) was added to a solution of N-methyl-2-methyl-2-dimethylamino hexylamine (0.754 g., 4.4 mmole) in dry benzene (25 ml.) and the solution heated under reflux for 1 hr. The cooled solution was washed with 2N sodium hydroxide solution (4 × 100 ml.), water (4 × 100 ml.), dried ($Na_2SO_4$) and evaporated to a colourless oil (1.612 g.). The oil was dissolved in benzene, chromatographed on a column of alumina (25 × 3.0 cm.) eluting with benzene/ether 1:1, and fractions (9 × 100 ml.) were collected. Fractions 2–8 were combined and, on evaporation, afforded 3,4-dichloro-N-methyl-N-[2-methyl-2-dimethylamino-hexyl]benzamide as a colourless oil (1.282 g., 84%).

3,4-Dichloro-N-Methyl-N-[2-Methyl-2-Dimethylamino-hexyl]benzamide Oxalate

A solution of oxalic acid (0.180 g., 2 mmole) in ethyl acetate (5 ml.) was added to a solution of 3,4-dichloro-N-methyl-N-[2-methyl-2-dimethylamino-hexyl]benzamide (0.69 g., 2 mmole) in ethyl acetate (5 ml.) and the solution oiiled for two mins. The solution was allowed to cool, and reduced in volume to ca. 5 ml., when a colourless oil began to separate. On leaving overnight, white crystals appeared, which were filtered, washed with ethyl acetate and dried to afford 3,4-dichloro-N-methyl-N-[2-methyl-2-dimethylamino-hexyl]benzamide oxalate (0.644 g., 76%), m.p. 130°–135° C.

EXAMPLE 90

1-Dimethylaminocyclohexylamide

1-Cyanocyclohexyldimethylamine (4 g., 9.26 mole) was heated on a steam bath with sulphuric acid (50 ml) for 10 min., cooled, the reaction mixture poured onto crushed ice (150 g), basified with ammonia and the alkaline material extracted with chloroform. The extract was washed with water, dried ($Na_2SO_4$), and evaporated under reduced pressure to give a colourless oil (3.2 g, 72.7%) which crystallised from light petroleum (b.p. 60°–80°) as colourless prisms of 1-dimethylaminocyclohexylamide m.p. 55°–56°.

EXAMPLE 91

1-Pyrrolidinycyclohexylamide 1-(1-Cyanocyclohexyl) pyrrolidine (2.0 g.) was heated on a steam bath with sulphuric acid (40 ml) for 10 min., cooled poured onto crushed ice (150 g.,), basified with ammonia and extracted with chloroform. The extract was washed with water, dried ($Na_2SO_4$), and evaporated to yield a colourless oil (1.75 g, 96.1%) which crystallised on cooling. Recrystallisation from light petroleum (b.p. 80°–100°) gave colourless plates of 1-pyrrolidinylcyclohexylamide m.p. 106°–107°.

EXAMPLE 92

1-(4-Methylpiperazinyl) cyclohexylamide 1-(1-Cyanocyclohexyl)-4-methylpiperazine (2.07 g, 0.01 mole) was heated on a steam bath with sulphuric acid (40 ml) for 0.25 hr., cooled, poured onto crushed ice (150 g.), basified with ammonia and the resulting mixture extracted with chloroform. The extract was washed with water, dried ($MgSO_4$), and evaporated under reduced pressure to give a viscous, amber oil (1.51 g, 67.7%) which crystallised from light petroleum (b.p. 80°–100°) to yield as colourless plates, 1-(4-methylpiperazinyl) cyclohexylamide, m.p. 107°.

EXAMPLE 93

1-Piperidylcyclopentylamide

1-Cyanocyclopentylpiperidine (1.78 g, 0.1 mole) was heated on a steam bath with sulphuric acid (40 ml) for 10 min., cooled, poured onto crushed ice (150 g), basified with ammonia and extracted with chloroform. The extract was washed with water, dried ($Na_2SO_4$), and evaporated to yield a colourless oil (1.6 g, 82.0%) which crystallised on cooling. Recrystallisation from light petroleum (b.p. 100°–120°) gave colourless plates of 1-piperidylcyclopentylamide, m.p. 112°–114°.

EXAMPLE 94

1-Dimethylamino cyclohexane carboxamide

1-Cyano-N,N-dimethyl cyclohexylamine (10 g.) was added portionwise to conc. sulphuric acid (20 ml.) and the solution left for 15 minutes. The cooled solution was diluted with ice-cold water and neutralized with barium hydroxide octahydrate. The mixture was filtered on hyflo and the filtrate evaporated to dryness when the residual oil (9.1 g., 81%) crystallised on standing. Recrystallisation from petrol (80/100) afforded 1-dimethylamino cyclohexane carboxamide m.p. 65°69°.

EXAMPLE 95

1-Dimethylamino-N-[3,4-dichlorotolyl]-cyclohexane carboxamide and its hydrochloride Sodium hydride (0.8 g., 50% dispersion in oil) was added to a solution of 1-dimethylaminocyclohexane carboxamide (2 g.) in dimethylformamide (40 ml.) and the mixture stirred for 2 hrs. A solution of 3,4-dichlorobenzyl chloride (2.4 g.) in dimethylformamide (10 ml.) was added dropwise and the resulting mixture stirred overnight. The mixture was filtered and the filtrate evaporated to dryness. Petrol (80/100) was added, the mixture boiled, and the solid filtered off. The filtrate was decolourised with activated charcoal and evaported to dryness to leave a colourless oil. The oil was dissolved in 2N hydrochloric acid and washed with benzene (4 × 200 ml.). The aqueous phase was basified (2N NaOH) and extracted with benzene (4 × 200 ml.). The benzene extracts were washed with water, (4 × 200 ml.) dried ($Na_2SO_4$) and evaporated to leave a colourless oil (2.1 g.), shown by T.L.C. (silica/ether) to consist of three components. The oil was dissolved in the minimum of ether and chromatographed on a column of silica (50 × 2.0 cms.) eluting with ether (11 × 100 ml. fractions). Fractions 3–11 were combined, evaporated to dryness and rechromatographed as above. Combination and evaporation of the appropriate fractions afforded a white crystalline solid (1.315 g., 35%). Recrystallisation from 40/60 petrol afforded 1-dimethylamino-N-[3,4-dichlorotolyl]-cyclohexane carboxamide as white needles (0.846 g.) m.p. 82°–83° C. A second crop (0.091 g.) melted at 78°–83° C.

1-Dimethylamino-N-[3,4-dichlorotolyl]-cyclohexane carboxamide (0.658 g.,) was dissolved in ethanol (5 ml.) and ethereal hydrogen chloride (10 ml.) was added. The solution was evaporated to leave a colourless oil which was taken up in the minimum volume of acetic acid. Dropwise addition of ether, with scratching and cooling, precipitated the hydrochloride as colourless prisms which was dried over potassium hydroxide in vacuo (0.688 g., m.p. 160°–170°). Recrystallisation from ethanol (addition of ether) afforded 1-dimethylamino-N-[3,4-dichlorotolyl]-cyclohexane carboxamide hydrochloride as white prisms (0.351 g., 48%); m.p. 162°–166° C.

What is claimed is:

1. A compound of the formula:

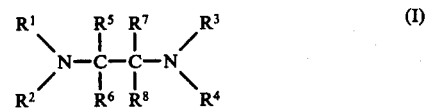

wherein $R^1$ represents a hydrogen atom; one of the acyl groups, formyl, acetyl, 4-fluorobenzoyl, 2-chlorobenzoyl, 3,4-dichloro benzoyl, 2,3,4-trimethoxy benzoyl, 4-nitro-benzoyl, 4-aminobenzoyl; ethoxycarbonyl, methyl or ethyl;

$R^2$ represents hydrogen or methyl;

$R^5$ and $R^6$ represent hydrogen;

$R^7$ and $R^8$ together form cyclohexyl; and $R^3$ and $R^4$ together with the adjacent nitrogen atom form a piperidyl group.

2. The compound of claim 1 which is 1-(2-chlorobenzamidomethylcyclohexyl) piperidine.

3. The compound of claim 1 which is [(1-piperidinocyclohexyl)methyl] carbamic acid, ethyl ester.

4. The compound of claim 1 which is 1-[1-(p-nitrobenzamidomethyl)cyclohexyl]-piperidine.

* * * * *